US009615809B2

(12) United States Patent
Lee et al.

(10) Patent No.: US 9,615,809 B2
(45) Date of Patent: Apr. 11, 2017

(54) TOMOGRAPHY APPARATUS AND METHOD OF DISPLAYING TOMOGRAPHY IMAGE BY TOMOGRAPHY APPARATUS

(71) Applicant: SAMSUNG ELECTRONICS CO., LTD., Suwon-si (KR)

(72) Inventors: Kyoung-yong Lee, Hwaseong-si (KR); Dong-jin Yang, Seoul (KR); Jong-hyon Yi, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 14/620,850

(22) Filed: Feb. 12, 2015

(65) Prior Publication Data

US 2015/0223771 A1  Aug. 13, 2015

(30) Foreign Application Priority Data

Feb. 12, 2014 (KR) .................. 10-2014-0016274
Jan. 16, 2015 (KR) .................. 10-2015-0008251

(51) Int. Cl.
| | |
|---|---|
| *G06K 9/00* | (2006.01) |
| *A61B 6/00* | (2006.01) |
| *A61B 6/03* | (2006.01) |
| *A61B 5/0245* | (2006.01) |
| *G06T 11/00* | (2006.01) |
| *A61B 5/00* | (2006.01) |

(Continued)

(52) U.S. Cl.
CPC ............ *A61B 6/541* (2013.01); *A61B 5/0044* (2013.01); *A61B 5/0245* (2013.01); *A61B 6/032* (2013.01); *A61B 6/463* (2013.01); *A61B 6/466* (2013.01); *A61B 6/503* (2013.01); *A61B 6/5205* (2013.01); *A61B 6/5235* (2013.01); *A61B 6/5264* (2013.01); *A61B 6/5288* (2013.01); *G06T 7/0002* (2013.01); *G06T 11/003* (2013.01); *G06T 11/008* (2013.01);
(Continued)

(58) Field of Classification Search
CPC ..................... G06T 2207/30048; A61B 6/541
See application file for complete search history.

(56) References Cited

U.S. PATENT DOCUMENTS

| | | | |
|---|---|---|---|
| 7,006,862 | B2 | 2/2006 | Kaufman et al. |
| 7,209,779 | B2 | 4/2007 | Kaufman et al. |

(Continued)

FOREIGN PATENT DOCUMENTS

| | | |
|---|---|---|
| KR | 100343215 B1 | 8/2002 |
| KR | 1020130138612 A | 12/2013 |
| KR | 101351583 B1 | 1/2014 |

OTHER PUBLICATIONS

Communication (PCT/ISA/210 and PCT/ISA/237) from the International Searching Authority, dated May 8, 2015 in a counterpart application No. PCT/KR2015/001379.

*Primary Examiner* — Bhavesh Mehta
*Assistant Examiner* — Oneal R Mistry
(74) *Attorney, Agent, or Firm* — Sughrue Mion, PLLC

(57) ABSTRACT

A tomography apparatus includes an image processor configured to reconstruct a tomography image by using pieces of image data that are acquired during partial periods included in a heartbeat period; and a display configured to display a screen image, which includes information representing the heartbeat period, and the reconstructed tomography image, and on which the partial periods and image sections corresponding to the partial periods are displayed in association with each other.

42 Claims, 39 Drawing Sheets

(51) Int. Cl.
*G06T 7/00* (2017.01)
*A61B 6/02* (2006.01)
*A61B 5/0452* (2006.01)

(52) U.S. Cl.
CPC ............. *A61B 5/0452* (2013.01); *A61B 6/027* (2013.01); *A61B 6/488* (2013.01); *A61B 6/5217* (2013.01); *A61B 2576/023* (2013.01); *G06T 2200/04* (2013.01); *G06T 2200/24* (2013.01); *G06T 2207/10081* (2013.01); *G06T 2207/30048* (2013.01); *G06T 2211/412* (2013.01)

(56) References Cited

U.S. PATENT DOCUMENTS

| | | | |
|---|---|---|---|
| 7,545,903 | B2 | 6/2009 | Kohler et al. |
| 2003/0016851 | A1* | 1/2003 | Kaufman ............ A61B 6/5264 382/131 |
| 2004/0125908 | A1* | 7/2004 | Cesmeli ................ A61B 6/032 378/4 |
| 2009/0161822 | A1* | 6/2009 | Hagiwara ............ A61B 6/032 378/20 |
| 2009/0232379 | A1* | 9/2009 | Kohler .................... G06T 7/20 382/131 |
| 2013/0190637 | A1* | 7/2013 | Zhang ................. A61B 5/0456 600/521 |
| 2013/0331697 | A1 | 12/2013 | Park et al. |
| 2014/0100441 | A1 | 4/2014 | Jo et al. |

\* cited by examiner

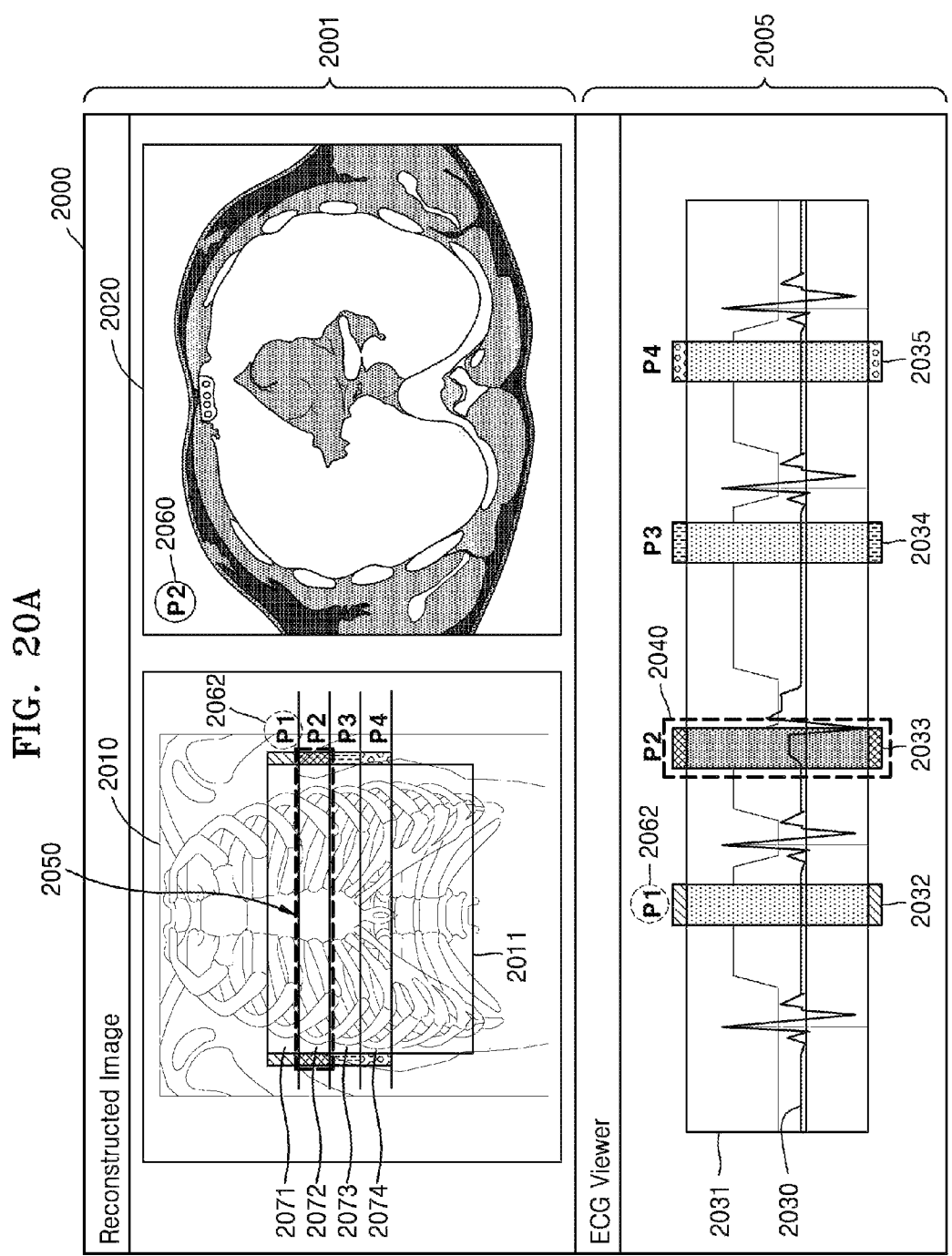

FIG. 20B
(a)
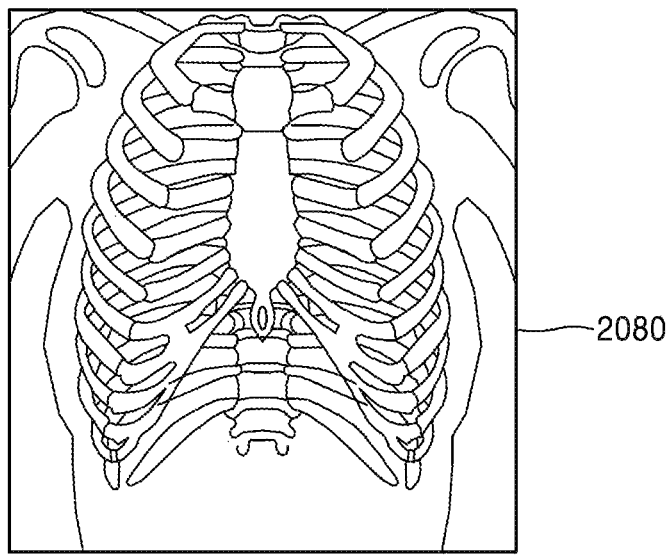
2080
(b)
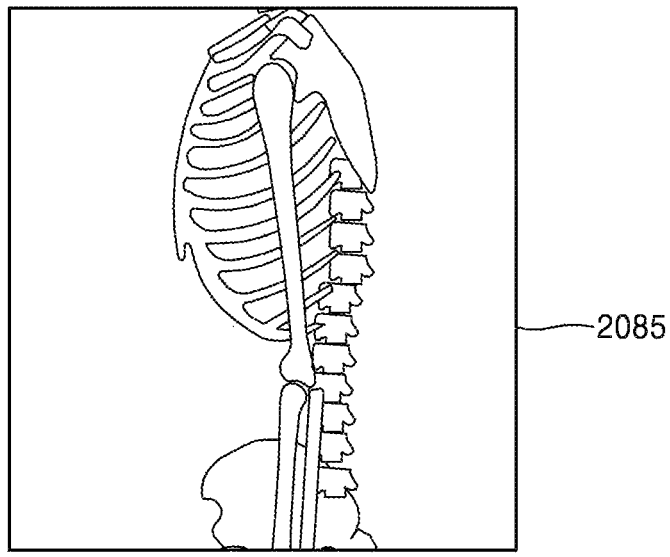
2085

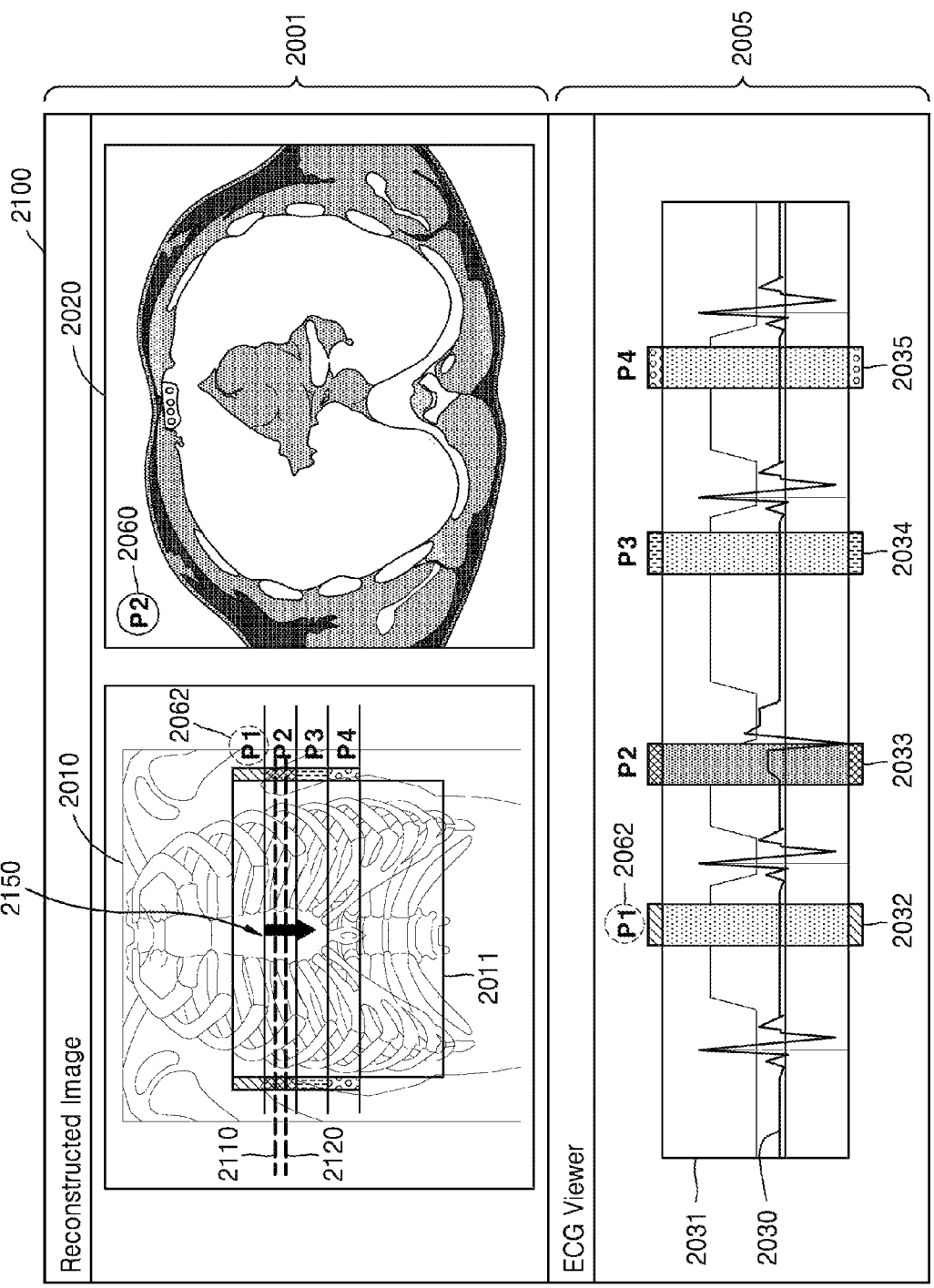

TOMOGRAPHY APPARATUS AND METHOD OF DISPLAYING TOMOGRAPHY IMAGE BY TOMOGRAPHY APPARATUS

CROSS-REFERENCE TO RELATED APPLICATIONS

This application claims priority from Korean Patent Application No. 10-2014-0016274, filed on Feb. 12, 2014, and Korean Patent Application No. 10-2015-0008251, filed on Jan. 16, 2015, in the Korean Intellectual Property Office, the disclosures of which are incorporated herein in their entireties by reference.

BACKGROUND

1. Field

Apparatuses and methods consistent with exemplary embodiments relate to displaying a tomography image by the tomography apparatus, and more particularly, to performing a tomography scan by using a heartbeat period and displaying a tomography image by the tomography apparatus.

2. Description of the Related Art

Medical imaging apparatuses are noninvasive medical examination apparatuses that capture images of the structural details of a human body, internal tissue thereof, and fluid flow within a human body, process the images, and show the processed images. A user such as a doctor may diagnose a health state and a disease of a patient by using a medical image output from a medical image processing apparatus.

A computed tomography (CT) apparatus acquires an image of an object by emitting radiation onto a patient and detecting the radiation having passed through the patient.

The CT apparatuses provide images which distinctly express an inner structure of organs such as a kidney, a lung, etc., of the object. Thus, the CT apparatuses are widely used in medical imaging.

During capturing of a tomography image, an artifact may be generated due to a motion of a patient. For example, when a heart is scanned by a tomography apparatus, a motion artifact may be generated due to a heartbeat.

To prevent the motion artifact, a method of reconstructing an image by using data that is acquired in consideration of a heartbeat may be used. In this case, data is acquired during sections between the peaks of the heartbeat period, and a final tomography image that represents the entire object is reconstructed using the acquired pieces of data.

However, often times, when an artifact is generated in the final tomography image corresponding to one or more sections acquired between the peaks of the heartbeat period, a user of a related art tomography apparatus cannot determine whether an artifact has been generated until the final tomography image is reconstructed and interpreted, and, thus, an entire CT scan protocol needs to be re-executed and a tomography image needs to be completely re-obtained.

Accordingly, when an artifact is generated, data acquired during previous CT scans cannot be used, and time loss and a reduced scanner throughput due to a re-scan occur, leading to inconvenience of medical personnel and patients.

Therefore, there is a need for apparatuses and methods for quickly determining that an artifact has been generated, during a CT scan, and easily correcting the artifact.

SUMMARY

Exemplary embodiments may address at least the above problems and/or disadvantages and other disadvantages not described above. Also, the exemplary embodiments are not required to overcome the disadvantages described above, and an exemplary embodiment may not overcome any of the problems described above.

One or more embodiments include a tomography apparatus capable of intuitively ascertaining a data section used to reconstruct a tomography image, and a tomography image displaying method performed by the tomography apparatus.

In detail, one or more exemplary embodiments include a tomography apparatus capable of quickly recognizing and easily correcting an artifact generated in a tomography image, and a tomography image displaying method performed by the tomography apparatus.

According to an aspect of an exemplary embodiment, a tomography apparatus includes an image processor configured to reconstruct a tomography image by using pieces of image data that are acquired during partial periods included in a heartbeat period; and a display configured to display a screen image, which includes information representing the heartbeat period, and the reconstructed tomography image, and on which the partial periods and image sections corresponding to the partial periods are displayed in associated with each other.

The display may display the screen image on which an image section of the reconstructed tomography image that corresponds to at least one of the partial periods is visually associated with the at least one partial period.

The tomography apparatus may further include a monitor configured to acquire information representing a result of monitoring an electrocardiogram (ECG) signal representing the heartbeat period.

The image processor may acquire the partial periods by windowing a phase section of the ECG signal by ECG gating and control the partial periods to be indicated by windows in the ECG signal and then displayed.

The tomography apparatus may further include an information provider configured to inform a user of a defect in response to the defect being present in the reconstructed tomography image.

The display may display the screen including a marker on at least one selected from a defective partial period, which is included in the partial periods and corresponds to a defect, and a defect-containing image section of the reconstructed tomography image, which has been reconstructed in correspondence to the defective partial period, under the control of the image processor.

In response to a defect being present in the reconstructed tomography image, the image processor may extract a defect-free partial period that would prevent generation of the defect in the reconstructed tomography image from the heartbeat period, and control the display to display a user interface (UI) image for recommending the extracted defect-free partial period to a user.

The tomography apparatus may further include a UI unit configured to receive a selection of the recommended defect-free partial period via the UI image. The image processor may reconstruct again an image portion corresponding to the defect-containing image section by using image data acquired during the selected defect-free partial period.

In response to a defect being present in the reconstructed tomography image, the image processor may automatically adjust a defective partial period corresponding to the defect, and automatically correct the defect-containing image section by using image data acquired during the adjusted partial period.

The tomography apparatus may further include a UI unit configured to output a menu for selecting another partial period instead of a defective partial period corresponding to a defect-containing image section of the reconstructed tomography image, and receive a selection of the another partial period via the menu. The image processor may automatically correct the defect-containing image section by using image data acquired during the selected another partial period.

The image processor may acquire pieces of projection data during the partial periods, reconstruct the partial images by using the pieces of projection data, and generate a final tomography image representing an object by using the partial images.

The tomography image may be a three-dimensional (3D) tomography image.

The image processor may acquire an initially reconstructed tomography image that is obtained based on the pieces of image data, and generate a final tomography image by correcting a defect generated in at least one image section included in the initially reconstructed tomography image.

The screen image may further include the final tomography image.

A tomography image included in the screen image may be the initially reconstructed tomography image and the final tomography image.

According to another aspect of an exemplary embodiment, a tomography apparatus includes an image processor configured to reconstruct a tomography image by using pieces of image data that are acquired during partial periods included in a heartbeat period, and, in response to a defect being present in the reconstructed tomography image, reconstruct again an image portion corresponding to a defect-containing image section of the reconstructed tomography image by using corrected image data acquired during another partial period which avoids a defect generation; and a display configured to display a screen image including the reconstructed tomography image including image sections, update the defect-containing image section of the reconstructed tomography image in real time with the corrected image data, and display an updated image section corresponding to a result of the updating.

In response to the defect being present in the reconstructed tomography image, the image processor may acquire position information of the another partial period, from the heartbeat period, and acquire the corrected image data based on the position information.

The display may display the screen image, which includes information representing the heartbeat period and the reconstructed tomography image and on which an image section of the reconstructed CT image that corresponds to at least one of the partial periods is displayed in association with the at least one partial period.

The display may display the screen image on which the updated image section is visually distinguished from the image sections which have not been updated.

The display may display a marker which identifies the updated image section on the screen image.

The display may display the screen image which includes information representing the heartbeat period, and the corrected partial period is marked within the information representing the heartbeat period, on the screen image.

The display may display the screen image on which the partial period corresponding to the defect is visually distinguished from the another partial period within the information representing the heartbeat period.

The tomography apparatus may further include a UI unit configured to output a menu image for recommending the another partial period and receive a selection of the recommended another partial period via the menu image, in response to the defect being present in the reconstructed tomography image.

The image processor may reconstruct again an image portion corresponding to the defect-containing image section by using the corrected image data acquired during the selected another partial period and generate an updated tomography image.

The tomography apparatus may further include a monitor configured to acquire information represents a result of monitoring an electrocardiogram (ECG) signal representing the heartbeat period.

According to another aspect of an exemplary embodiment, a tomography image displaying method includes reconstructing a tomography image by using pieces of image data that are acquired during partial periods included in a heartbeat period; and displaying a screen image that includes information representing the heartbeat period and the reconstructed tomography image and on which the partial periods and image sections of the reconstructed CT image that correspond to the partial periods are displayed such that they are associated with each other.

The tomography image displaying method may further include ascertaining that a defect has been generated in the reconstructed CT image; extracting, from the heartbeat period, a defect-free partial period that prevents generation of a defect in the reconstructed tomography image, in response to the defect generated in the reconstructed tomography image; and outputting a UI image for recommending the extracted defect-free partial period to a user.

The tomography image displaying method may further include automatically adjusting a defective partial period corresponding to a defect-containing image section, in response to a defect being present in the reconstructed tomography image; and automatically correcting the defect-containing image section by using image data acquired during the adjusted partial period.

According to another aspect of an exemplary embodiment, a tomography image displaying method includes reconstructing an initial tomography image by using pieces of image data that are acquired during partial periods included in a heartbeat period; displaying a screen image including the reconstructed initial tomography image; reconstructing again an image portion corresponding to a defect-containing image section of the reconstructed initial tomography image by using corrected image data acquired from another partial period which would prevent generating a defect, in response to the defect being present in the reconstructed initial tomography image; updating the defect-containing image section with a reconstructed-again image portion; and displaying a result of the updating.

According to another aspect of an exemplary embodiment, a tomography apparatus includes an image processor configured to reconstruct a tomography image corresponding to a predetermined region of a medical image including an object, by using pieces of image data that are acquired during partial periods included in a heartbeat period; and a display configured to display a screen image, which includes the medical image and information representing the heartbeat period and on which the partial periods and image sections of the predetermined region that correspond to the partial periods are displayed such that they are associated with each other.

The screen image may further include a sectional tomography image included in the reconstructed tomography image.

The reconstructed tomography image may be a transverse cross-sectional tomography image.

The medical image may be a scout image that represents an entire object, and the sectional tomography image may be a cross-sectional image included in the reconstructed tomography image.

The scout image may be an anteroposterior or lateral scout image, and the sectional tomography image may be a transverse cross-sectional tomography image.

The screen image may visually associate the partial image with an image section of the predetermined region that corresponds to the partial image.

The screen image may visually associate the partial image with a respective partial period corresponding to the partial image.

The tomography apparatus may further include a UI unit configured to receive at least one of a predetermined portion or a point selected from the predetermined portion and a partial period selected from the partial periods. The image processor may control a tomography image included in the reconstructed tomography image and corresponding to the selected point or the selected partial period to be displayed on the screen image.

As the tomography image is being reconstructed, the reconstructed tomography image may be updated in real time and an updated tomography image may be displayed on the screen image.

The screen image may visually associate the updated tomography image with an image section of the predetermined region that corresponds to the updated tomography image.

The screen image may visually associate the updated tomography image with one of the partial periods corresponding to the updated tomography image.

A current tomography image that is the updated tomography image and a previous tomography image that is reconstructed prior to the updated tomography image may be displayed on the screen image so that the previous tomography image is overlaid with the current tomography image.

The screen image may further include a 3D tomography image corresponding to the reconstructed tomography image, and the screen image may show the partial periods and image sections included in the 3D tomography image that correspond to the partial periods such that they are associated with each other.

BRIEF DESCRIPTION OF THE DRAWINGS

The above and/or other aspects will become more apparent by describing certain exemplary embodiments, with reference to the accompanying drawings, in which:

FIG. 20A illustrates another screen image displayed by the tomography apparatus according to an exemplary embodiment;

FIG. 20B is a view for explaining a scout image;

FIG. 21 illustrates another screen image displayed by the tomography apparatus according to an exemplary embodiment;

DETAILED DESCRIPTION

Figure 1A:
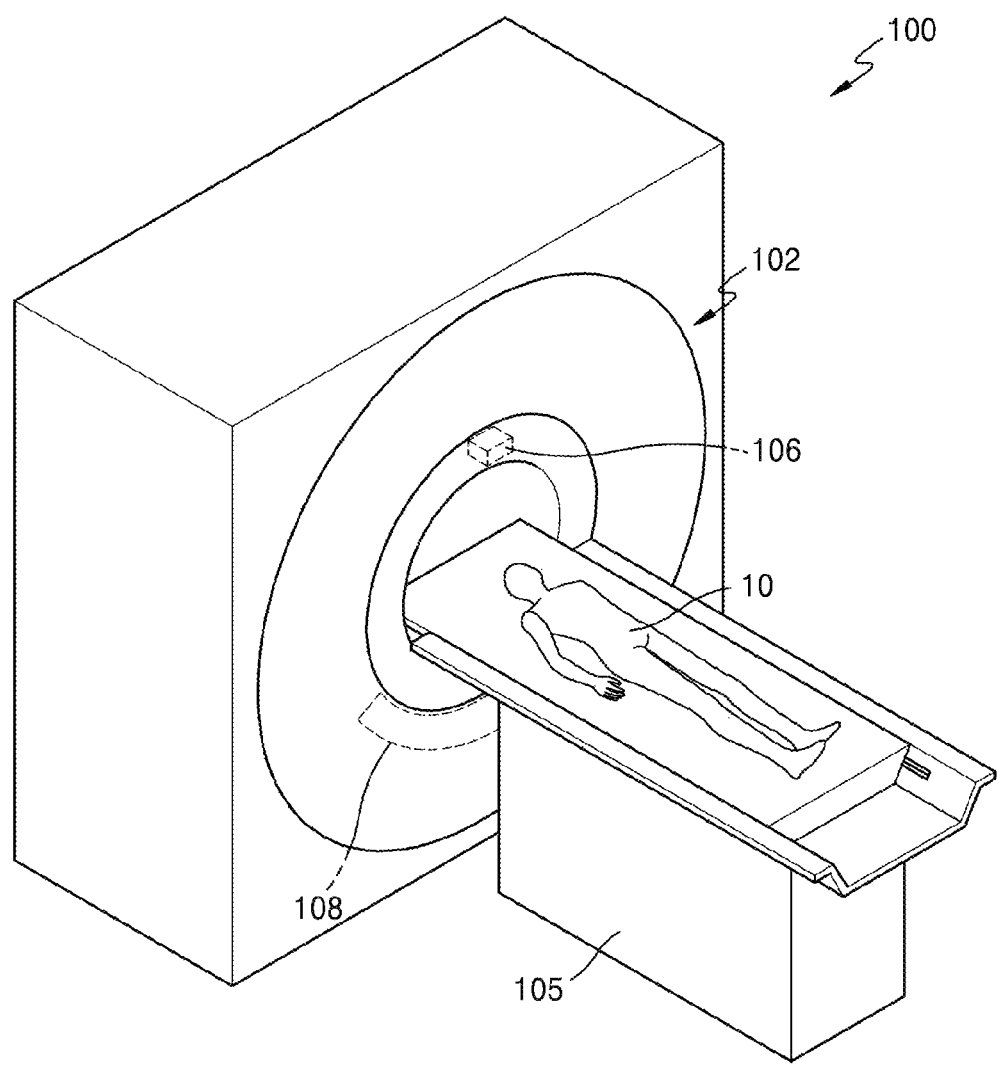
FIG. 1A is a schematic view of a CT system according to an exemplary embodiment.

Certain exemplary embodiments are described in greater detail below with reference to the accompanying drawings.

In the following description, the same drawing reference numerals are used for the same elements even in different drawings. The matters defined in the description, such as a detailed construction and elements, are provided to assist in a comprehensive understanding of exemplary embodiments. Thus, it is apparent that exemplary embodiments can be carried out without those specifically defined matters. Also, well-known functions or constructions are not described in detail since they would obscure exemplary embodiments with unnecessary detail.

The terms "comprises" and/or "comprising" or "includes" and/or "including" when used in this specification, specify the presence of stated elements, but do not preclude the presence or addition of one or more other elements. Also, the term 'unit' in the embodiments of the present invention means a software component or hardware components such as a field-programmable gate array (FPGA) or an application-specific integrated circuit (ASIC), and performs a specific function. However, the term 'unit' is not limited to software or hardware. The term 'unit' may be configured to be included in an addressable storage medium or to reproduce one or more processors. Thus, for example, the term 'unit' may refer to components such as software components, object-oriented software components, class components, and task components, and may include processes, functions, attributes, procedures, subroutines, segments of program code, drivers, firmware, micro codes, circuits, data, a database, data structures, tables, arrays, or variables. A function provided by the components and 'units' may be associated with the smaller number of components and 'units', or may be divided into additional components and 'units'.

Throughout the specification, an image may mean multi-dimensional data formed of discrete image elements (e.g., pixels in a two-dimensional (2D) image and voxels in a 3D image). For example, the image may include a medical image of an object which is captured by a CT apparatus.

A tomography image is an image acquired by a tomography apparatus scanning an object, namely, may mean an image obtained by projecting light, such as X-rays, to the object and imaging the object by using projection data. A CT image may mean a cross-sectional image generated by synthesizing a plurality of X-ray images that are obtained by imaging an object while a CT apparatus rotates around at least one axis with respect to the object. A CT image may also mean a 3D tomography image generated by synthesizing cross-sectional images.

An object may include a human, an animal, or a part of a human or animal. For example, the object may include organs such as the liver, the heart, the womb, the brain, a breast, the abdomen, etc., or a blood vessel. Also, the object may include a phantom. The phantom means a material having a volume that is very close to a density and effective atomic number of an organism, and may include a sphere phantom having a characteristic similar to a physical body.

A user may be, but is not limited thereto, a medical expert, such as a doctor, a nurse, a health care technician, or a medical imaging expert, or may be an engineer who manages medical appliances.

For example, the tomography system 100 may include any of tomography apparatuses, such as a computed tomography (CT) apparatus, an optical coherence tomography (OCT) apparatus, or a positron emission tomography (PET)-CT apparatus.

A case where the tomography system 100 is a CT system will now be described.

The CT system may obtain a plurality of pieces of image data with a thickness no more than 2 mm for several tens to several hundreds of times per second and then may process the plurality of pieces of image data, thereby providing a relatively accurate cross-sectional image of the object. According to the related art, only a horizontal cross-sectional image of the object can be obtained, but this issue has been overcome due to various image reconstruction methods. Examples of 3D image reconstruction methods include:

A shaded surface display (SSD) method: The SSD method is an initial 3D imaging method that only displays voxels having a predetermined Hounsfield Units (HU) value.

A maximum intensity projection (MIP)/minimum intensity projection (MinIP) method: The MIP/MinIP method is a 3D imaging method that only displays voxels having the greatest or smallest HU value from among voxels that construct an image.

A volume rendering (VR) method: The VR method is an imaging method capable of adjusting a color and transmittance of voxels that construct an image, according to interest areas.

A virtual endoscopy method: This method allows an endoscopy observation in a 3D image that is reconstructed by using the VR method or the SSD method.

A multi planar reformation (MPR) method: The MPR method is used to reconstruct an image into a different cross-sectional image. A user may reconstruct an image in every desired direction.

An editing method: This method involves editing adjacent voxels so as to allow a user to easily observe an interest area in volume rendering.

A voxel of interest (VOI) method: The VOI method is used to only display a selected area in volume rendering.

A CT system 100 according to an exemplary embodiment will now be described with reference to FIG. 1A.

FIG. 1A is a block diagram of the CT system 100 which may include a gantry 102, a table 105, an X-ray generator 106, and an X-ray detector 108.

An object 10 may be positioned on the table 105.

The table 105 may move in a predetermined direction (e.g., at least one of up, down, right, and left directions) during a CT scan. Also, the table 105 may tilt or rotate by a predetermined angle in a predetermined direction.

The gantry 102 may also tilt by a predetermined angle in a predetermined direction.

Figure 1B:
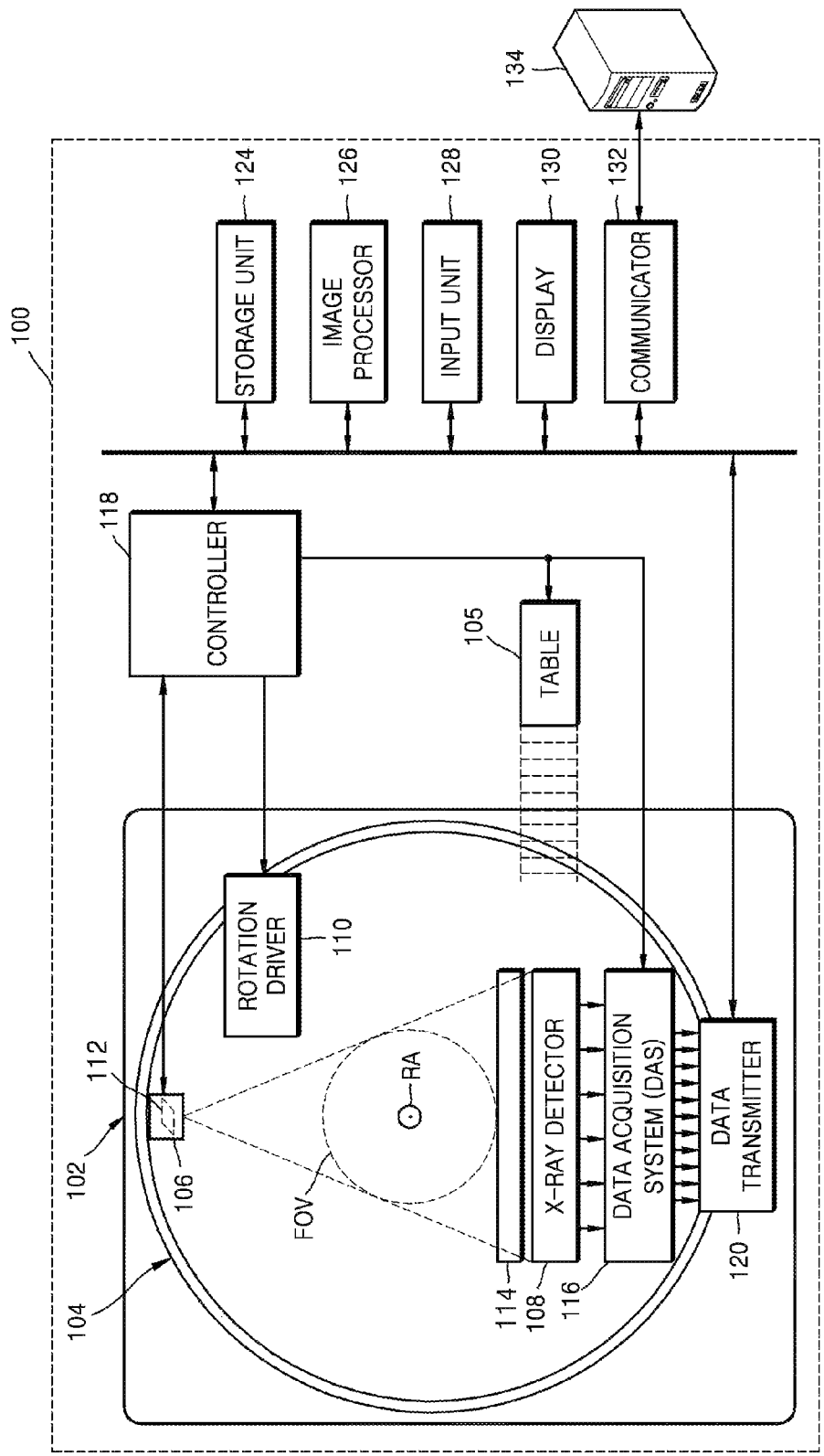
FIG. 1B illustrates a structure of the CT system according to an exemplary embodiment.

FIG. 1B illustrates a detail of the CT system 100.

The CT system 100 may include a controller 118, a storage unit 124, an image processor 126, an input unit 128, a display 130, and a communicator 132.

The gantry 102 may include a rotating frame 104, the X-ray generator 106, the X-ray detector 108, a rotation driver 110, a data acquisition system (DAS) 116, and a data transmitter 120.

The gantry 102 may include the rotating frame 104 having a loop shape capable of rotating with respect to a predetermined rotation axis RA. The rotating frame 104 may have a disc shape.

The rotating frame 104 may include the X-ray generator 106 and the X-ray detector 108 that face each other to have predetermined field of views (FOV). The rotating frame 104 may also include an anti-scatter grid 114 positioned between the X-ray generator 106 and the X-ray detector 108.

In a medical imaging system, X-ray radiation that reaches a detector (or a photosensitive film) may include attenuated primary radiation that forms a valuable image and scattered radiation that deteriorates a quality of an image. In order to transmit the primary radiation and to block the scattered radiation, the anti-scatter grid 114 may be positioned between a patient and the detector (or the photosensitive film).

For example, the anti-scatter grid 114 may be formed by alternately stacking lead foil strips and an interspace material such as a solid polymer material, solid polymer, or a fiber composite material. However, formation of the anti-scatter grid 114 is not limited thereto.

The rotating frame 104 may receive a driving signal from the rotation driver 110 and may rotate the X-ray generator 106 and the X-ray detector 108 at a predetermined rotation speed. The rotating frame 104 may receive the driving signal and power from the rotation driver 110 while the rotating frame 104 contacts the rotation driver 110 via a slip ring (not shown). Also, the rotating frame 104 may receive the driving signal and power from the rotation driver 110 via wireless communication.

The X-ray generator 106 may receive a voltage and current from a power distribution unit (PDU) (not shown) via a slip ring (not shown) and a high voltage generator (not shown). When the high voltage generator applies a predetermined voltage (hereinafter, referred as the tube voltage) to the X-ray generator 106, the X-ray generator 106 may generate and emit X-rays having a plurality of energy spectrums that correspond to the tube voltage.

A width of the X-ray generated by the X-ray generator 106 may be adjusted by a collimator 112.

The X-ray detector 108 may include a plurality of X-ray detecting devices. Each of the plurality of X-ray detecting devices may establish one channel, but an exemplary embodiment is not limited thereto.

The X-ray detector 108 may detect the X-ray that is generated by the X-ray generator 106 and that is transmitted via the object 10, and may generate an electrical signal corresponding to the intensity of the detected X-ray.

The X-ray detector 108 may include an indirect-type X-ray detector for detecting radiation after converting the radiation into light, and a direct-type X-ray detector for detecting radiation after directly converting the radiation into electric charges. The indirect-type X-ray detector may use a scintillator. The direct-type X-ray detector may use a photon counting detector. The DAS 116 may be connected to the X-ray detector 108. Electrical signals generated by the X-ray detector 108 may be collected by the DAS 116 in a wired or wireless manner. The electrical signals generated by the X-ray detector 108 may be provided to an analog-to-digital converter (not shown) via an amplifier (not shown).

A digital signal may be provided to the image processor 126 via the data transmitter 120 in a wired or wireless manner.

According to a slice thickness or the number of slices, only some of a plurality of pieces of data collected by the X-ray detector 108 may be provided to the image processor 126 via the data transmitter 120, or the image processor 126 may select only some of the plurality of pieces of data.

The controller 118 may control an operation of the elements in the CT system 100. For example, the controller 118 may control operations of the table 105, the rotation driver 110, the collimator 112, the DAS 116, the storage unit 124, the image processor 126, the input unit 128, the display 130, the communicator 132, and the like.

The image processor 126 may receive data obtained from the DAS 116 (e.g., data before a processing operation), via the data transmitter 120, and may perform pre-processing.

The pre-processing may include a process of correcting sensitivity irregularity between channels, a process of correcting a signal loss due to a rapid decrease of signal strength or due to an X-ray absorbing material such as metal, or the like.

Data output from the image processor 126 may be referred as raw data or projection data. The projection data may be stored together with image-capturing conditions (e.g., the tube voltage, an image-capturing angle, etc.), in the storage unit 124.

The projection data may be a group of data values that correspond to the intensity of the X-ray that has passed through the object 10. For convenience of description, a group of a plurality of pieces of projection data that are simultaneously obtained from all channels by a same image-capturing angle is referred as a projection data set.

The storage unit 124 may include at least one storage medium selected from a flash memory, a hard disk, a multimedia card (MMC) micro, card memory (for example, a secure digital (SD) or extreme digital (XD) memory), random access memory (RAM), static random access memory (SRAM), read-only memory (ROM), electrically erasable programmable ROM (EEPROM), programmable ROM (PROM), magnetic memory, a magnetic disk, and an optical disk.

The image processor 126 may reconstruct a cross-sectional image with respect to the object 10 by using the projection data set. The cross-sectional image may be a 3D image. In other words, the image processor 126 may reconstruct a 3D image of the object 10 by using a cone beam reconstruction method or the like, based on the obtained projection data set.

The input unit 128 may receive an external input with respect to an X-ray tomography imaging condition, an image processing condition, or the like. For example, the X-ray tomography imaging condition may include a plurality of tube voltages, energy value setting with respect to a plurality of X-rays, selection of an image-capturing protocol, selection of an image reconstruction method, setting of a FOV area, the number of slices, a slice thickness, setting of image post-processing parameters, or the like. The image processing condition may include resolution of an image, attenuation coefficient setting with respect to the image, setting of an image combining ratio, or the like.

The input unit 128 may include a device for receiving a predetermined input from an external source. For example, the input unit 128 may include a microphone, a keyboard, a mouse, a joystick, a touch pad, a touch pen, a voice recognition device, a gesture recognition device, or the like.

The display 130 may display an X-ray tomography image reconstructed by the image processor 126.

Exchanges of data, power, or the like between the aforementioned elements may be performed by at least one of wired communication, wireless communication, and optical communication.

The communicator 132 may perform communication with an external device, an external medical apparatus, etc., via a server 134 or the like.

Figure 1C:
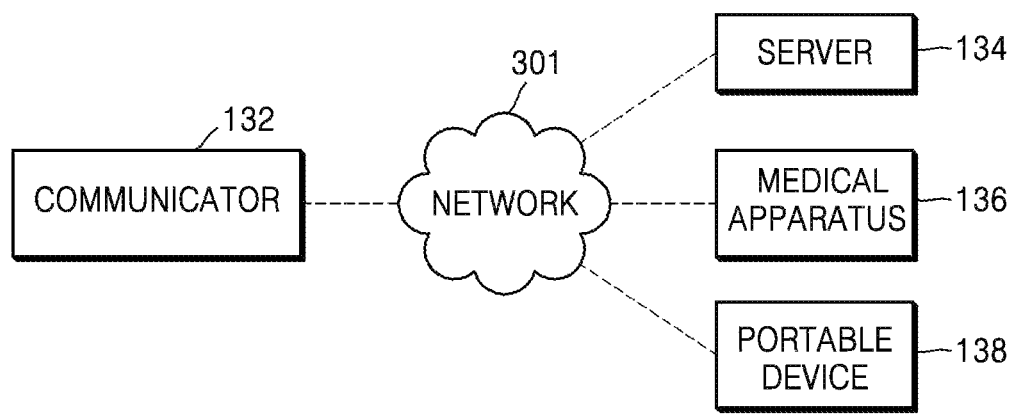
FIG. 1C is a diagram for illustrating a communicator included in the CT system according to an exemplary embodiment.

FIG. 1C is a diagram for illustrating communications of the communicator 132.

The communicator 132 may be connected to a network 301 in a wired or wireless manner and may perform communication with the server 134, an external medical apparatus 136, or an external portable device 138. The communicator 132 may exchange data with a hospital server or other medical apparatuses in a hospital connected via a Picture Archiving and Communication System (PACS).

Also, the communicator 132 may perform data communication with the portable device 138 or the like of a user or a patient, according to a Digital Imaging and Communications in Medicine (DICOM) standard.

The communicator 132 may transmit and receive data related to diagnosing the object 10, via the network 301. Also, the communicator 132 may transmit and receive a medical image obtained from the medical apparatus 136 such as a magnetic resonance imaging (MRI) apparatus, an X-ray apparatus, or the like.

Furthermore, the communicator 132 may receive a medical history or a medical treatment schedule about a patient from the server 134 and use the same to diagnose the patient.

The communicator 132 may transmit information about a device error, information about a quality control status, or the like to a system manager or a service manager via the network 301, and may receive a feedback corresponding to the information.

Figure 2:
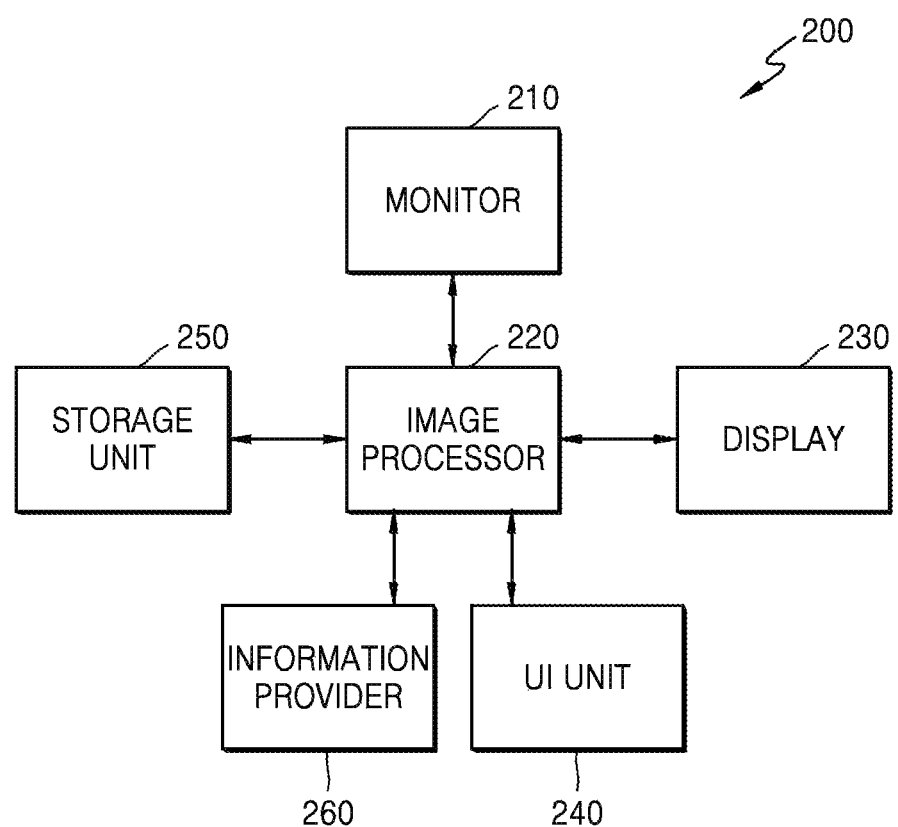
FIG. 2 is a block diagram of a tomography apparatus according to an exemplary embodiment.

FIG. 2 is a block diagram of a tomography apparatus 200 according to an exemplary embodiment. Referring to FIG. 2, the tomography apparatus 200 includes an image processor 220, and a display 230. The tomography apparatus 200 may be included in the CT system 100 described above with reference to FIGS. 1A and 1B. Alternatively, the tomography apparatus 200 may be included in the medical apparatus 136 or the portable device 138 of FIG. 1C and may be connected to the CT system 100 to operate.

For example, the tomography apparatus 200 may be any of medical imaging apparatuses that reconstruct images by using the data acquired by using a light beam that has passed through an object. In other words, the tomography apparatus 200 may be any medical imaging apparatus that reconstructs images by using projection data obtained by using a light beam that has passed through an object and/or displays the reconstructed images. For example, the tomography apparatus 200 may be a CT apparatus, an OCT apparatus, or a PET-CT apparatus. Accordingly, a tomography image obtained by the tomography apparatus 200 according to the present embodiment may be a CT image, an OCT image, or a PET image. In the drawings referred to the following descriptions, a CT image is exemplified as the tomography image.

When the tomography apparatus 200 is included in the CT system 100, the image processor 220 and the display 230 may correspond to the image processor 126 and the display 130 of FIG. 1B, respectively, and repeated descriptions will be omitted.

The tomography apparatus 200 may further include at least one of a monitor 210, a user input (UI) unit 240, a storage unit 250, and an information provider 260.

The image processor 220 and the storage unit 250 may correspond to the input unit 128 and the storage unit 124 of FIG. 1B, respectively, and repeated descriptions will be omitted.

The monitor 210 acquires information representing a heartbeat period of a patient. For example, the monitor 210 monitors a cycle and rhythm of a heartbeat of the patient or information about a motion of the heart of the patient. For example, the monitor 210 may continuously acquire information about a portion of the heartbeat period when a motion of the heart is minimal. The monitor 210 may acquire information representing a heartbeat period of a heart, or receive, from an external source, the information representing a heartbeat period of a heart.

For example, the monitor 210 may acquire information representing a result of monitoring an ECG signal representing the heartbeat period of a heart. For example, the monitor 210 may be formed as an ECG recorder (not shown) to acquire an ECG signal. The monitor 210 may receive an ECG signal from an externally connected ECG recorder (not shown).

The monitor 210 may acquire various types of bio-signals representing a motion of a heart. As another example, the monitor 210 may acquire a heart Doppler signal and extract the time when a motion of the heart is minimal.

The monitor 210 may acquire information including all types of bio-signals representing a motion of a portion of an object that is to be scanned. For example, when abdomen CT is performed, the monitor 210 may acquire information representing a motion of heart incurred by breathing. For example, the monitor 210 may measure and monitor an ECG signal.

The image processor 220 reconstructs a tomography image by using a plurality of pieces of image data that are acquired during a plurality of partial periods included in the heartbeat period.

The heart of a patient who is to be scanned continuously moves. Due to the motion of the heart during the tomography scan, a motion artifact may be generated in the tomography image. The motion artifact causes an error within the reconstructed tomography image, and thus a user such as a doctor may inaccurately interpret a medical image.

Accordingly, during tomography image capturing, data is acquired during each time period when a motion of the heart is minimized, and the tomography image is reconstructed using the acquired data.

Therefore, the image processor 220 may reconstruct a CT image by using a plurality of pieces of image data that are acquired during at least one partial period that is included in the heartbeat period and in which a motion of the heart is minimal. The image data may be projection data, which is raw data. When the rotating frame 104 of FIG. 1B images an object while rotating the X-ray detection unit 108 at regular angles, the image data may be a sinogram acquired by accumulating pieces of projection data respectively acquired at different angles belonging to a predetermined angle range, for example, from 0 to 180 degrees.

The display 230 displays a screen image that includes information representing the heartbeat period and a tomography image and on which at least one of the partial periods and a section of the tomography image corresponding to the partial period are shown in association with each other. For example, the display 230 displays a screen image on which at least one of the partial periods and a section of the tomography image that corresponds to the at least one partial period are displayed such that they are visually associated with each other.

Screen images displayed on the display 230 according to embodiments will be described in more detail with reference to FIGS. 7 through 28.

The UI unit 240 generates and outputs a UI image for receiving a command or data from a user, and receives command or data from a user via the UI image. The UI image output by the UI unit 240 is output to the display 230 which may display the UI image. The user may identify information from the UI image displayed by the display 230 and may input a command or data via the UI mage.

For example, the UI unit 240 may include a mouse, a keyboard, or an input device including hard keys for inputting predetermined data. For example, the user may input data or a command by manipulating at least one of a mouse, a keyboard, and other input devices included in the UI unit 240.

The UI unit 240 may be a touch pad. For example, the UI unit 240 includes a touch pad (not shown) coupled with a display panel (not shown) included in the display 230 and outputs the UI image to the display panel. When a command is input via the UI image, the touch pad may sense the input operation and recognize the command input by the user.

For example, when the UI unit 240 is a touch pad and the user touches a certain point on the UI image, the UI unit 240 senses the touched point. Then, the UI unit 240 may transmit sensed information to the image processor 220. Thereafter, the image processor 220 may identify a user's request or command corresponding to a menu shown on the sensed point and may perform the user's request or command.

The storage unit 250 may store a plurality of pieces of image data acquired during a tomography scan. For example, the storage unit 250 may store a plurality of pieces of image data that are used in reconstructing a tomography image. For example, the storage unit 250 may store projection data. The storage unit 250 may also store various kinds of data, programs, and the like necessary for reconstructing a tomography image, and may store a finally-reconstructed tomography image.

The information provider 260 informs the user of predetermined data or information. For example, the information provider 260 may include at least one of a speaker, a light emitting diode (LED) lamp, and an alarm lamp.

When a defect is generated in a reconstructed tomography image, the information provider 260 may output a signal informing that a defect has been generated.

The information provider 260 may include any of information providing devices that output a signal that enables a user to recognize generation of a defect by using his or her sense of at least one of hearing, vision, and tough. For example, the information provider 260 may include a speaker (not shown) to output a sound message that informs generation of a defect. The information provider 260 may include a vibration motor to output a physical vibration signal that informs generation of a defect.

A tomography apparatus according to an embodiment of the present invention may acquire image data according to various scan modes or scanning methods. Examples of the scan modes used for a tomography scan may include a prospective mode and a retrospective mode, which will be described below in detail with reference to FIGS. 2 and 3. Examples of the scanning methods used for a tomography scan include an axial scanning method and a helical scanning method, which will now be described in detail with reference to FIGS. 2 and 3. The CT system 100 of FIGS. 1A and 1B may perform a tomography scan according to scanning methods and scan modes which will now be described with reference to FIGS. 3 and 4.

Figure 3:
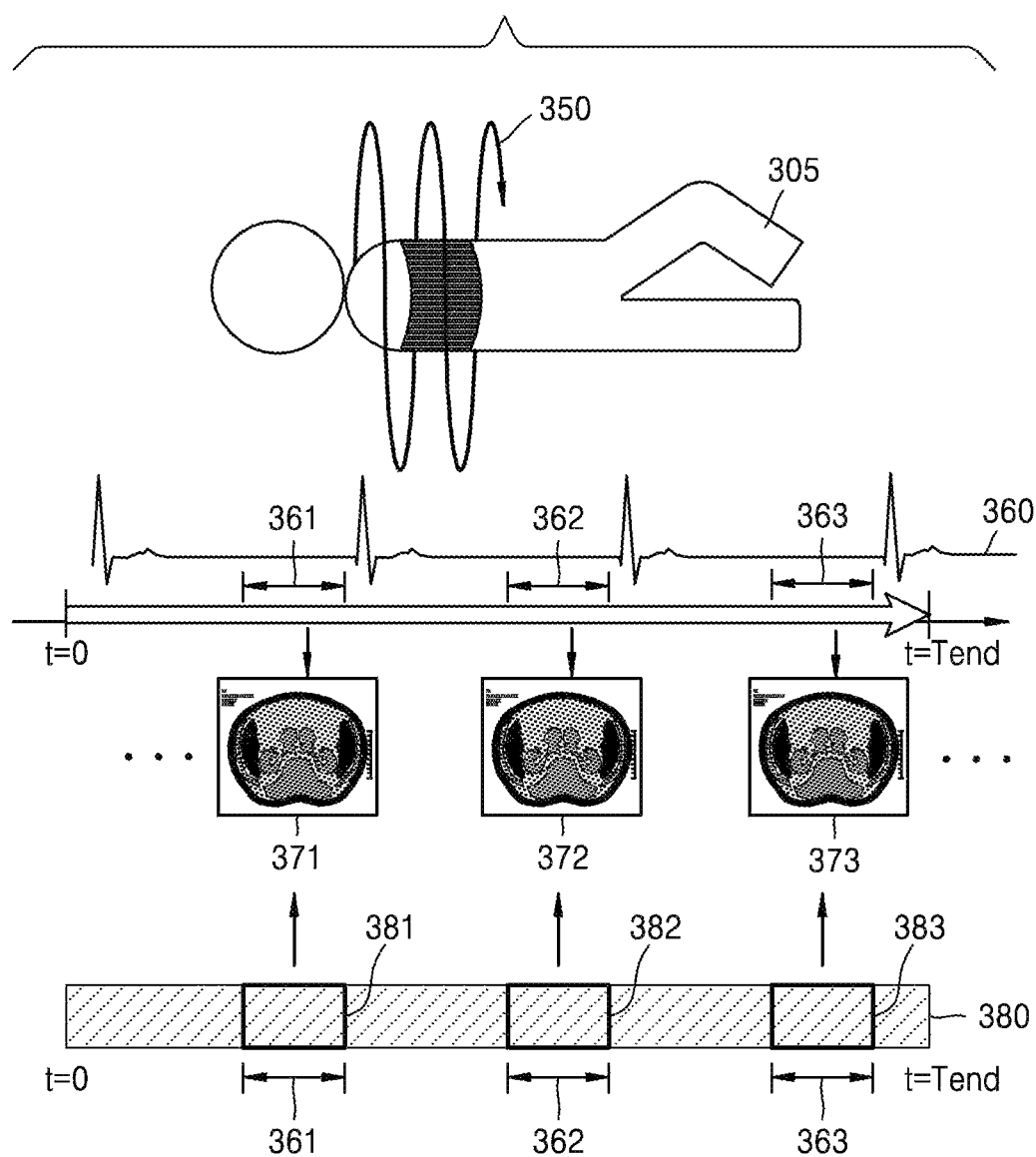
FIG. 3 is a view for explaining a scanning method that is used in a tomography scan according to an embodiment of the present invention.

FIG. 3 is a view for explaining a scanning method that is used in a tomography scan according to an embodiment of the present invention.

FIG. 3 is a view for describing a tomography scan according to a helical scanning method. Additionally, FIG. 3 is a view for describing a tomography scan according to a retrospective mode.

The scan mode may be determined according to whether a heart beat rate of a patient that is subject to imaging is constant or not. Electrocardiographic (ECG) gating may be used to acquire raw data that is used for reconstruction of an image. In FIGS. 3 and 4, while a tomography scan is performed, the table 105 of FIG. 1B is moved in an axial direction of a patient 305.

Referring to FIG. 3, the helical scanning method is a tomography method in which X-rays are continuously projected for scanning while the table 105 of FIG. 1B is moved during a predetermined period of time from t=0 to t=end. In detail, a tomography scan is performed by continuously moving, for a predetermined period of time at a predetermined speed, the table 105 of FIG. 1B on which the patient 305 including the object is laid and continuously projecting X-rays to the object while the table 105 is moving. Accordingly, a motion trajectory 350 of the X-rays may be a helix form.

Referring to FIG. 3, when a heart beat rate of a patient is irregular, as in the case of an arrhythmia patient, regularity of a heart beat rate is degraded and thus it is impossible to detect the cycle at regular intervals as in the prospective mode. In this case, an ECG signal 360 is irregularly gated in the retrospective mode. In the retrospective mode, raw data is acquired by radiating X-rays in all cycles of ECG signals or in consecutive predetermined cycles of ECG signals, and then partial cycles for tomography image reconstruction are selected.

In the retrospective mode, after a user individually sets partial cycles for use in image reconstruction to detect partial cycles 361, 362, and 363, the user uses pieces of raw data respectively acquired during the detected partial cycles 861, 862, and 863 in tomography image reconstruction. In other words, the image processor 220 may reconstruct a tomography image by using raw data 381 acquired during the partial period 361, raw data 382 acquired during the partial period 362, and raw data 383 acquired during the partial period 363, which are included in data 380. For example, the image processor 220 may reconstruct a tomography image representing the object at a predetermined time point included in the partial period 361, by using the raw data 381 acquired during the partial period 361, and may reconstruct a tomography image representing the object at a predetermined time point included in the partial period 362, by using the raw data 382 acquired during the partial period 362.

For example, in the retrospective mode, X-rays are continuously projected for a certain period of time from t=0 to t=end, thereby performing a tomography scan. Since the table 105 of FIG. 1B continuously moves at a predetermined speed for a predetermined period time, the motion trajectory 350 of the X-rays is in a helix form.

Figure 4A:
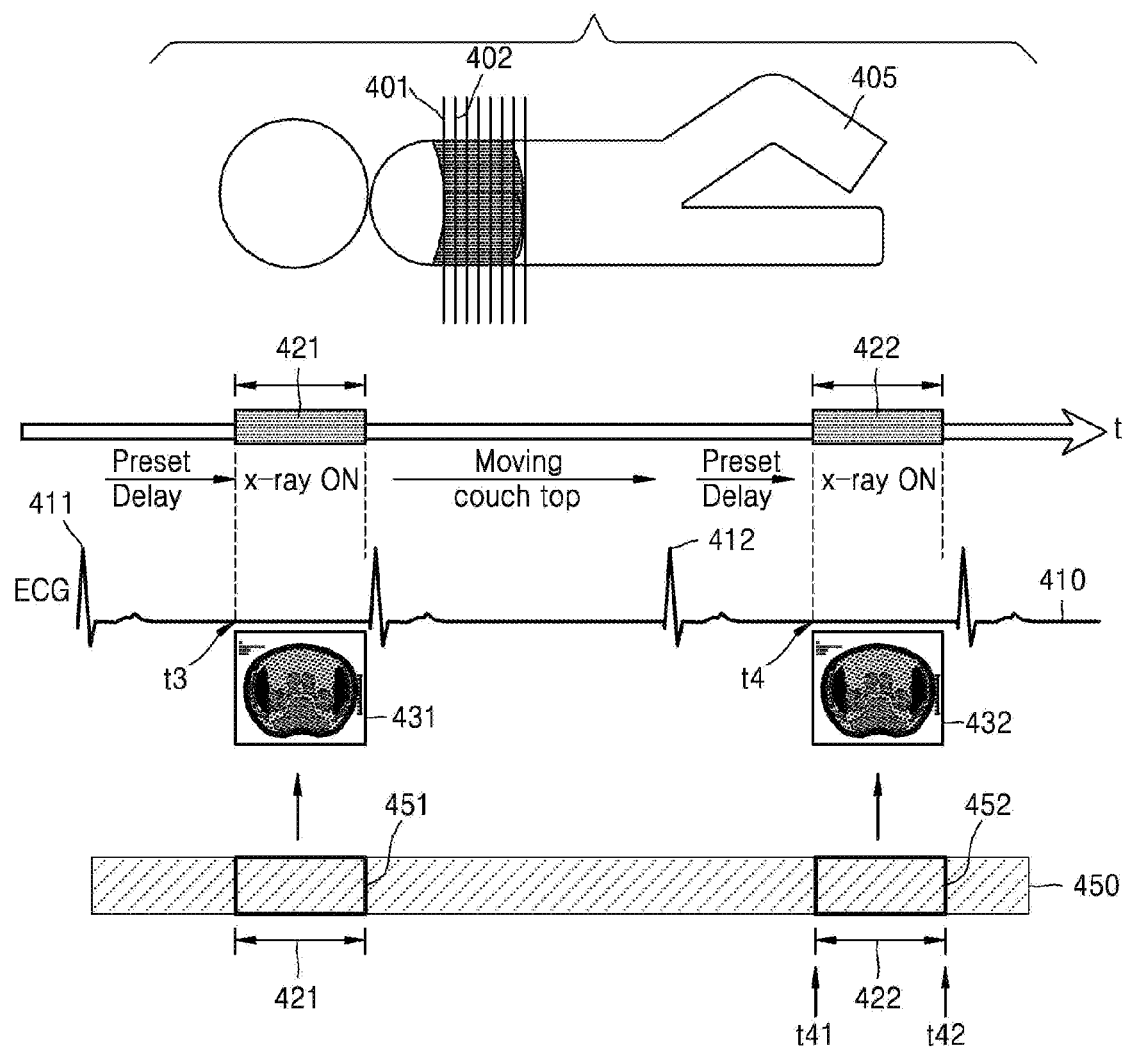
FIGS. 4A and 4B are views for explaining another scanning method that is used in a tomography scan according to an embodiment of the present invention.
Figure 4B:
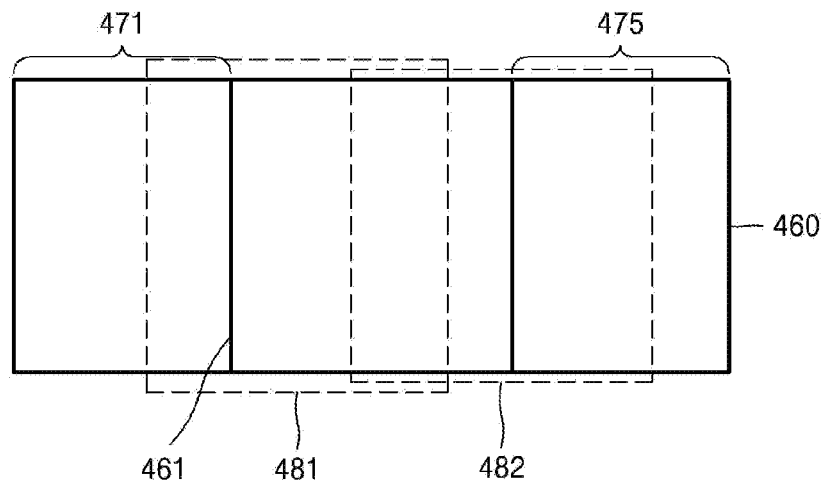

FIGS. 4A and 4B are views for explaining another scanning method that is used in a tomography scan according to an embodiment of the present invention.

Referring to FIG. 4A, the axial scanning method is a tomography method in which X-rays are projected for scanning while the table 105 of FIG. 1B is stopped, the table 105 is moved by a predetermined interval from 401 to 802, and then X-rays are projected for a predetermined section 422, thereby obtaining raw data. The tomography apparatus 200 may acquire image data according to the axial scanning method.

Referring to FIG. 4A, for a person having a constant heart beat rate, an ECG signal 410 is regularly gated by employing a prospective mode. In the prospective mode, a predetermined section 421, which is at a time point t3 spaced apart from an R peak 411 by a predetermined time period, is automatically selected or extracted. X-rays are applied to an object during the gated predetermined section 421 to acquire raw data. In the prospective mode, the predetermined section 422, which is at a time point t4 spaced apart from an R peak 412 by a predetermined time period, is automatically selected. At this time, X-rays are projected for scanning while the table 105 of FIG. 1B is stopped, the table 105 is moved by the predetermined interval from 401 to 402, and then X-rays are projected for the predetermined section 422, thereby obtaining raw data.

Referring to FIG. 4B, a length direction of image data 460 acquired in a selected or extracted section (e.g., the predetermined section 421 or 422) corresponds to time. In other words, the image data 460 may be data acquired during a time period from a time point t41 to a time point t42. In general, more pieces of data than image data necessary for tomography image reconstruction are acquired. For example, when the amount of the image data necessary for tomography image reconstruction is a first data amount 461, data may be further acquired in a first padding period 471, and data may be further acquired in a second padding period 475.

Figure 5:
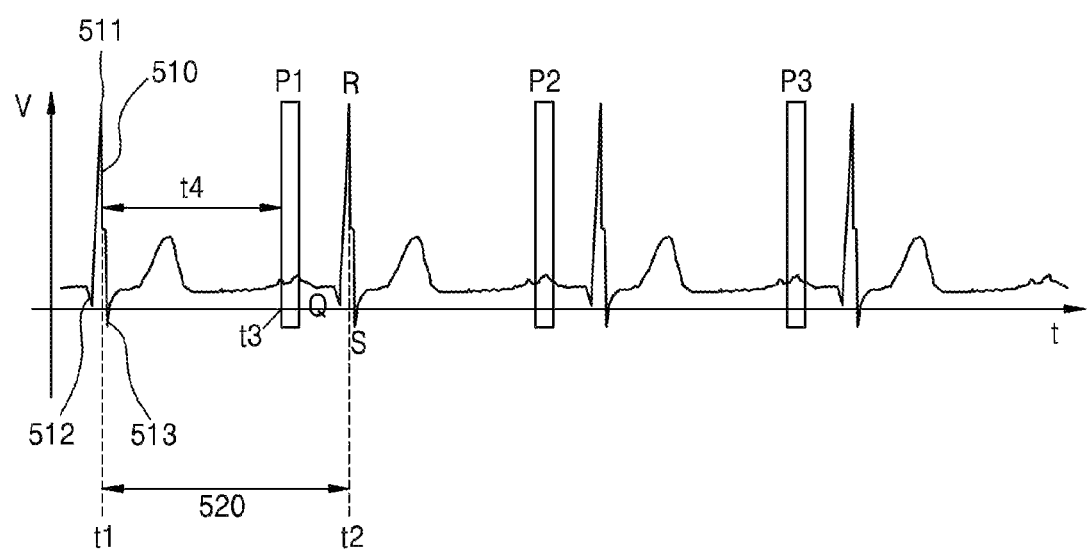
FIG. 5 illustrates an ECG signal.

In a tomography scan, for a patient having an irregular heart beat rate, a tomography scan may be performed by applying the retrospective mode to the helical scanning method. For a patient having a regular heart beat rate, a tomography scan may be performed by applying the prospective mode to the axial scanning method. However, embodiments of the present invention are not limited thereto and a tomography scan may be performed by applying the prospective mode to the helical scanning method or by applying the retrospective mode to the axial scanning method. FIG. 5 illustrates an ECG signal 510.

The heart supplies the blood to the body by periodic contractions. A heartbeat period of the heart may be determined based on an electrical signal generated by the heart. For example, an electrical signal generated by a sinoauricular node in the heart may be determined via an ECG examination in which an electrical signal from the heart is detected by electrodes attached to the surface of the skin. The detected electrical signal is represented as a graph, i.e., an ECG signal. The ECG signal includes cycle information of the heartbeat period. By analyzing the ECG signal, the user may ascertain an interval when a motion of the heart is minimal and may also ascertain whether the rhythm of the heart is irregular, fast, or slow.

Accordingly, the image processor 220 may use the ECG signal to reduce generation of a motion artifact in a tomography image during a CT scan. For example, by using the ECG signal, the tomography apparatus 200 may acquire a partial period when a motion of the heart is minimal, and may reconstruct a tomography image by using image data acquired during the acquired partial period. An operation of selecting a portion of a period from an ECG signal and acquiring image data from the selected period portion (hereinafter, referred to as a partial period) as described above is referred to as ECG gating.

For example, the image processor 220 windows a predetermined phase section of the ECG signal 510 by ECG gating to thereby acquire a plurality of partial periods P1 and P2. The image processor 220 may control a plurality of partial periods of the ECG signal to be windowed and displayed.

In FIG. 5, the x-axis represents time, and the y-axis represents a voltage by which a magnitude of the ECG signal is expressed.

Referring to FIG. 5, the ECG signal 510 includes several singularities in each cycle 520. For example, an R peak 511, a Q peak 512, and an S peak 513 may be included in the cycle 520. In the heartbeat period, an interval between a point in time t1 when an R peak is generated and a point in time t2 when a next R peak is generated may be referred to as the cycle 520.

An operating mode of ECG gating may vary depending on whether a cardiac cycle is constant. For example, when a cardiac cycle of a person is constant, the ECG signal 510 is gated in a prospective mode. In the prospective mode, the image processor 220 automatically selects the predetermined phase section P1, which is at a point in time t3 spaced apart from the R peak 511 by a predetermined period of time t4. In other words, in the prospective mode, after the R peak 511 is detected in each cycle, the predetermined sections at points in time spaced apart from the detected R peaks by a predetermined period of time for each point in time are detected, and pieces of image data acquired during only the detected predetermined sections are used in reconstructing a tomography image.

As another example, when a cardiac cycle is not constant as in an arrhythmia patient, regularity of the cardiac cycle is reduced, and thus uniform period detection as in the prospective mode is not be possible. The image processor 220 gates the ECG signal 510 in a retrospective mode. In the retrospective mode, image data is acquired by radiating X-ray in all cycles of the ECG signal 510 or consecutive cycles of a certain range, and then partial periods for image reconstruction are partially selected. In other words, in the retrospective mode, after a user sets partial periods which are to be used in image reconstruction and then detects the partial periods P1 and P2, the user uses image data acquired during the detected partial periods P1 and P2 in tomography image reconstruction.

Figure 6A:
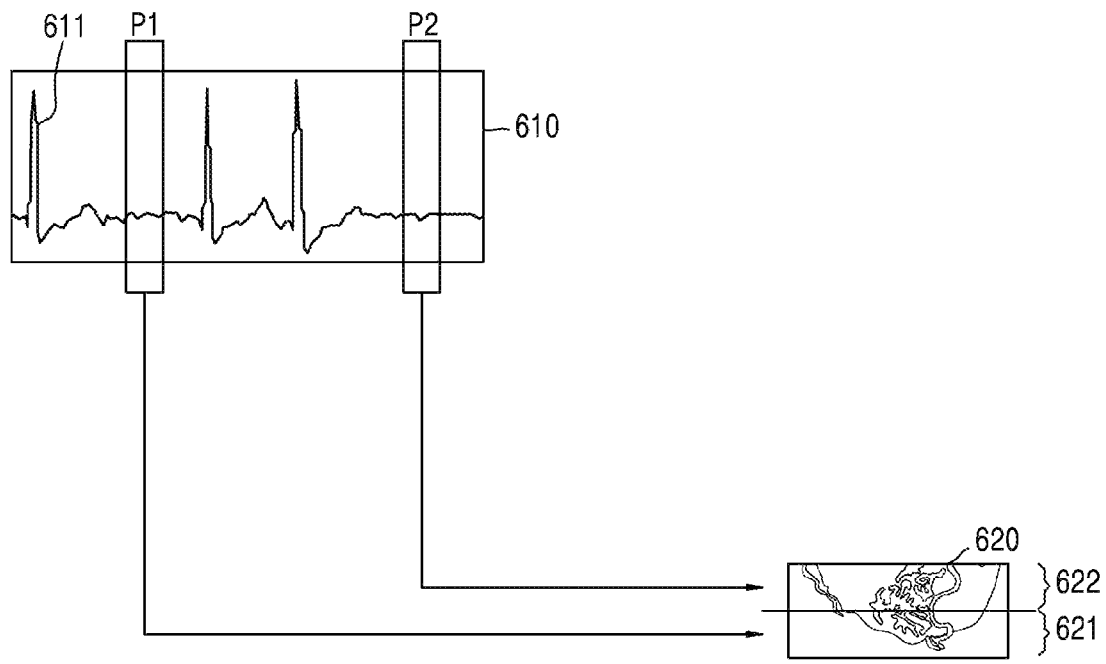
FIGS. 6A and 6B are schematic diagrams for describing tomography image reconstruction according to an exemplary embodiment.
Figure 6B:
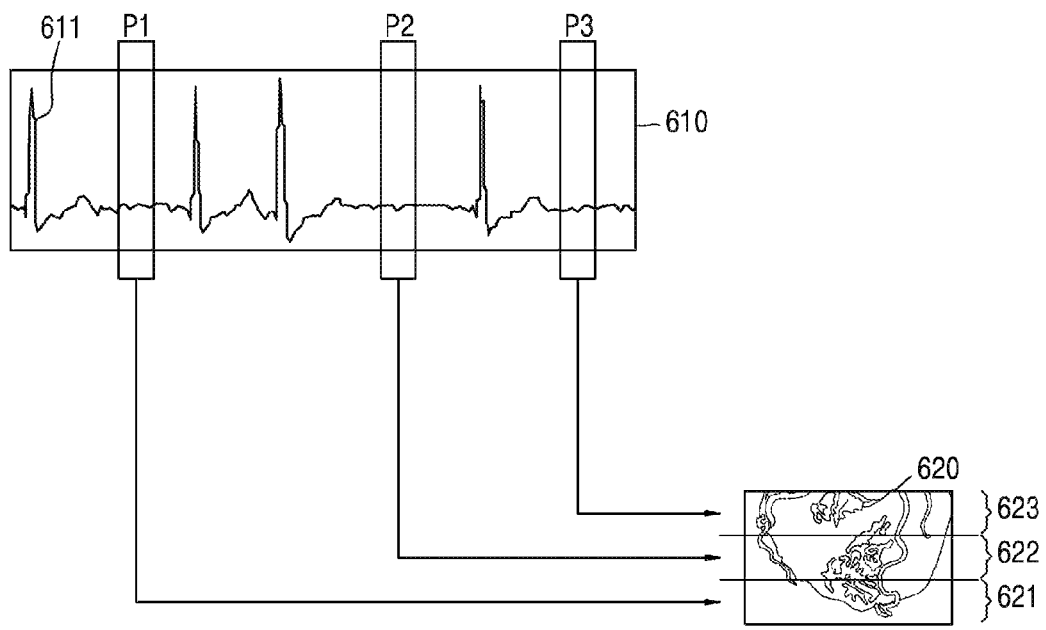

FIGS. 6A and 6B are schematic diagrams for describing CT image reconstruction according to an exemplary embodiment.

FIGS. 6A and 6B illustrate an operation in which the image processor 220 reconstructs a tomography image by using pieces of image data acquired during a plurality of partial periods.

Referring to FIG. 6A, the image processor 220 reconstructs each section of a tomography image by using pieces of image data respectively acquired during partial periods P1 and P2 detected from an ECG signal 611.

In a portion 610, an ECG signal that is monitored and partial periods are illustrated. In a portion 620, a reconstructed image is illustrated.

For example, referring to FIG. 6A, a first image section 621 in a tomography image is reconstructed using the image data acquired during the partial period P1, for example, projection data.

Then, the partial period P2 is gated after the partial period P1, and a second image section 622 adjacent to the first image section 621 is reconstructed using the image data acquired during the gated partial period P2.

Although the first image section 621 is reconstructed using the image data acquired during the single partial period P1 and the second image section 622 is reconstructed using the image data acquired during the single partial period P2 in FIG. 6A, the image processor 220 may reconstruct the first image section 621 or the second image 622 by using pieces of image data respectively acquired during a plurality of partial periods (for example, the partial periods P1 and P2).

Referring to FIG. 6B, after the reconstruction of the second image section 622, a partial period P3 is gated, and a third image section 623 adjacent to the second image section 622 is further reconstructed using image data acquired during the gated partial period P3.

Figure 7A:
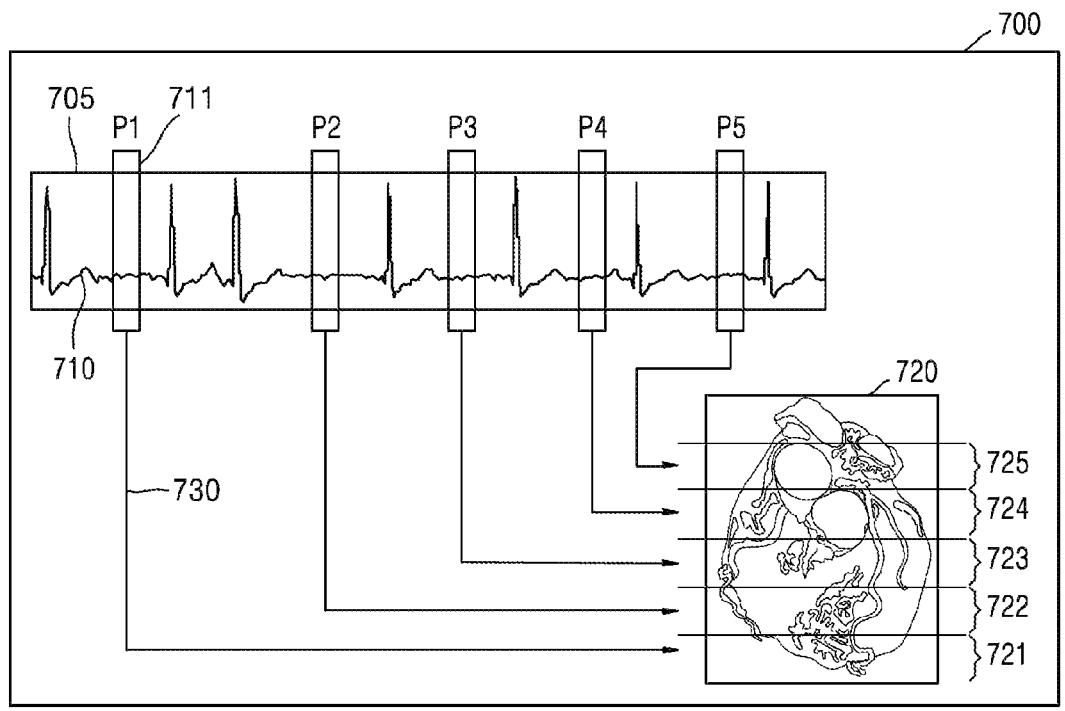
FIGS. 7A and 7B illustrate screen images displayed by the tomography apparatus according to an exemplary embodiment.
Figure 7B:
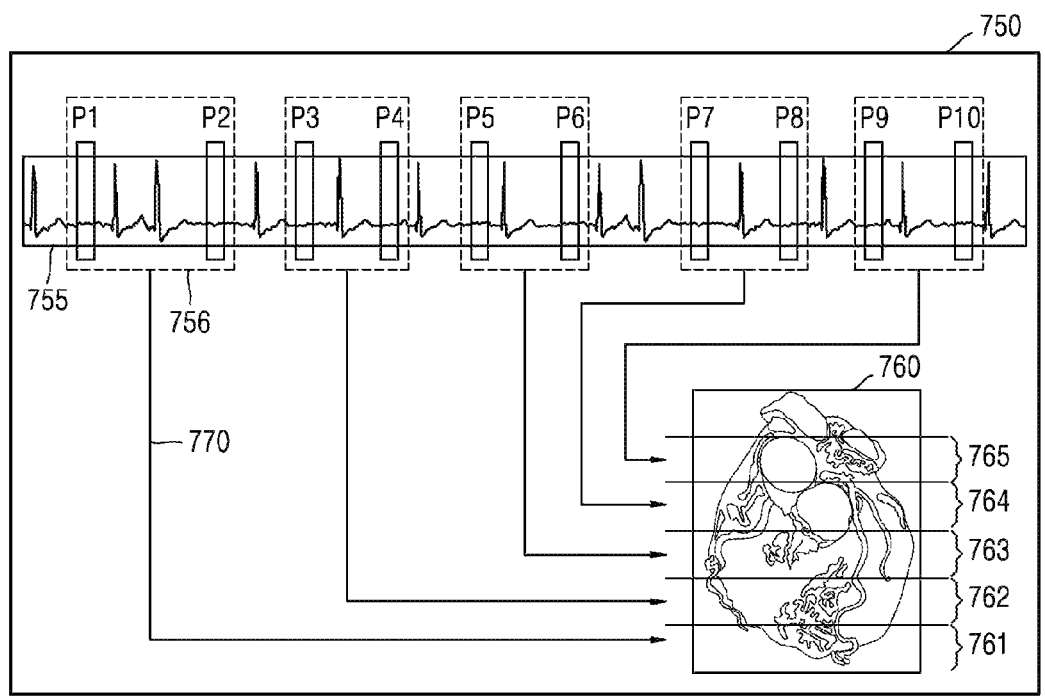

FIGS. 7A and 7B are screen images 700 and 750, respectively, displayed by the display 230.

The display 230 displays an image on which a plurality of partial periods and tomography image sections corresponding to the partial periods are shown in associated with each other. For example, the display 230 displays the plurality of partial periods and the tomography image sections such that at least one of a plurality of partial periods is associated with an image section corresponding to the partial period.

The reconstructed tomography image may be a 3D tomography image that expresses an object three-dimensionally. The 3D tomography image may be reconstructed to represent various views such as an anteroposterior view, a lateral view, and a transaxial view.

Referring to FIG. 7A, the screen image 700 includes information 705 representing a heartbeat period, and a tomography image 720. An ECG signal 710 is the information 705 representing the heartbeat period. In FIG. 7A, the tomography image 720 represents the entire heart, as an imaging object. However, the tomography image 720 may be a tomography image representing a portion of the heart, as the imaging object.

A plurality of partial periods P1, P2, P3, P4, and P5 and first, second, third, fourth, and fifth image sections 721, 722, 723, 724, and 725, respectively, of the tomography image 720 are displayed in association with each other.

The image processor 220 may control each of the partial periods P1, P2, P3, P4, and P5 of the ECG signal 710 to be marked with a window 711 and displayed.

For example, the image processor 220 may reconstruct a single image section by using image data acquired during a single partial period.

For example, the image processor 220 reconstructs the first image section 721 by using image data acquired during the partial period P1, reconstructs the second image section 722 by using image data acquired during the partial period P2, and reconstructs the third image section 723 by using image data acquired during the partial period P3. The image processor 220 reconstructs the fourth image section 724 by using image data acquired during the partial period P4 and reconstructs the fifth image section 725 by using image data acquired during the partial period P5.

Display of a partial period and an image section corresponding to the partial period in association with each other means that the partial period and the image section corresponding to the partial period are displayed so that a user may easily recognize that they are associated with each other. For example, as illustrated in FIG. 7A, to represent association between partial periods and corresponding image sections, the screen image 700 may visually connect the partial periods to image sections corresponding thereto via connecting lines 730. Association between partial periods and image sections corresponding thereto may be indicated using a same color, a same frame shape, a same marker, a same icon, a same pattern, or the like.

For example, a frame of the partial period P1 and a frame of the first image section 721 may be expressed in a same color, a same pattern, or a same shape. A frame of the partial period P2 and a frame of the second image section 722 may be displayed in a same color, a same pattern, or a same shape. The partial periods may be displayed using different colors, different frame shapes, different markers, different icons, different patterns, or the like. For example, when the partial period P1 and the first image section 721 are displayed to have red frames, the partial period P2 and the second image section 722 may be displayed to have orange frames.

Referring to FIG. 7B, the screen image 750 includes information 755 representing a heartbeat period, and a tomography image 760.

A plurality of partial periods P1 through P10 included in a heartbeat period, and first, second, third, fourth, and fifth image sections 761, 762, 763, 764, and 765 of the tomography image 760 are displayed in association with each other.

For example, the image processor 220 may reconstruct a single image section by using image data acquired from a plurality of partial periods.

For example, the image processor 220 reconstructs the first image section 761 by using image data acquired during the partial periods P1 and P2, reconstructs the second image section 762 by using image data acquired during the partial periods P3 and P4, and reconstructs the third image section 763 by using image data acquired during the partial periods P5 and P6. The image processor 220 reconstructs the fourth image section 764 by using image data acquired during the partial periods P7 and P8 and reconstructs the fifth image section 765 by using image data acquired during the partial periods P9 and P10.

As illustrated in FIG. 7B, the screen image 750 may display the mapping between partial periods and their corresponding image sections by using connecting lines 770. The partial periods P1 and P2 corresponding to the single image section 761 may be defined by a block 756 on the screen image 750, and the same relationship may be applied to the other partial periods P3 through P10.

Figure 8A:
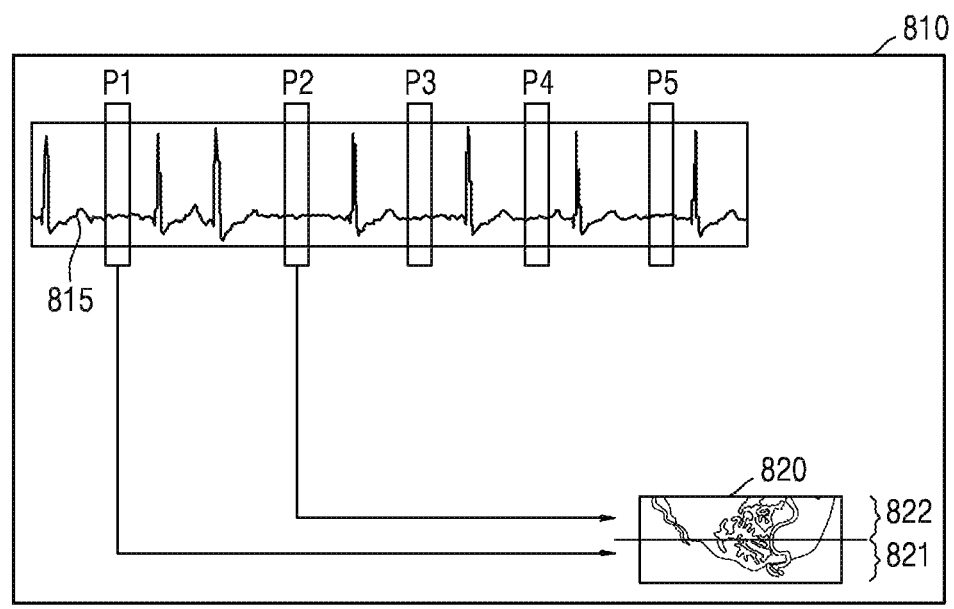
FIGS. 8A, 8B, and 8C illustrate other screen images displayed by the tomography apparatus according to an exemplary embodiment.
Figure 8B:
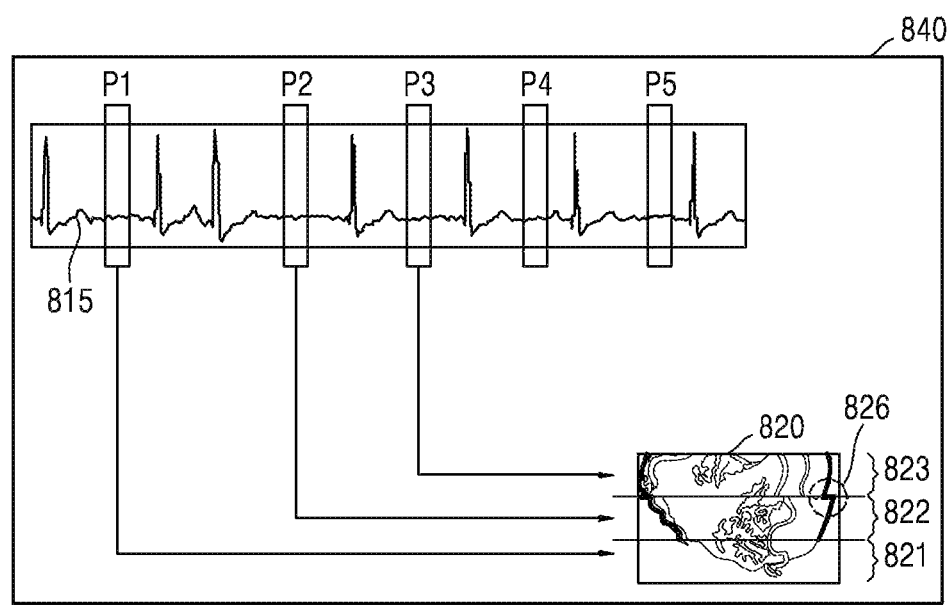
Figure 8C:
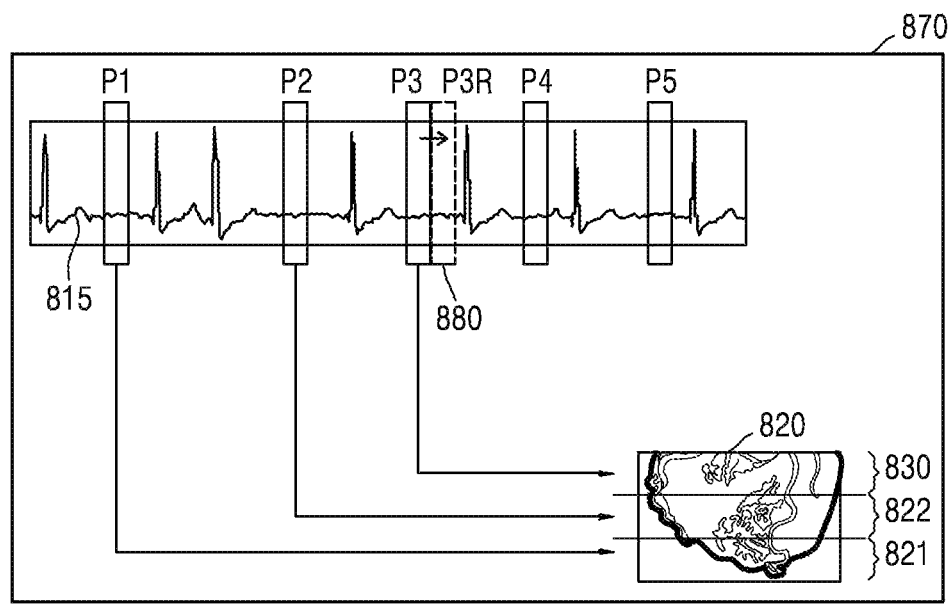

FIGS. 8A, 8B, and 8C are screen images 810, 840, and 870, respectively, displayed by the tomography apparatus 200 of FIG. 2.

The image processor 220 may control a partial image reconstruction for each partial period included in the heartbeat period to be updated in real time and displayed.

Referring to FIG. 8A, a first image section 821 in a tomography image is reconstructed using image data, for example, projection data, acquired during a partial period P1 of an ECG signal 815, and then a second image section 822 adjacent to the first image section 821 is reconstructed using image data acquired during a partial period P2 that is gated after the partial period P1.

The display 230 displays the screen image 810 representing an image section that is reconstructed for each partial period in real time. For example, as an image is reconstructed for each partial period in real time, the image processor 220 may control the screen image 810 of FIG. 8A and the screen image 840 of FIG. 8B to be displayed.

Referring to FIG. 8B, after the reconstruction of the second image section 822, a third image section 823 adjacent to the second image section 822 is reconstructed using image data acquired during a partial period P3 gated after the partial period P2.

After the screen image 810 is displayed, the display 230 may display the screen image 840 including an image section that has been reconstructed in real time after the reconstruction of the second image section 822.

When an image defect is generated in a reconstructed image section, the image processor 220 may correct the image section having the image defect and display a corrected image section.

The image defect is any image error that disturbs image interpretation of a user.

Examples of the image defect may include a volume gap, a stair artifact, mismatch of tissue included in an object, an image blur, and the like. As illustrated in FIG. 8B, a volume gap or a stair artifact denotes overall mismatch between objects included in the third image section 823 and the second image section 822 adjacent to each other. For convenience of explanation, a boundary mismatch, such as a volume gap or a stair artifact in an image, will now be referred to as a stair artifact.

When discontinuity appears on tissue included in an object, for example, the coronary arteries, it may be determined that an artifact has been generated in an image of the object.

For example, the image processor 220 may extract and track a blood vessel, coronary arteries, or the like, and check whether discontinuity has been generated in the tracked detailed object, thereby determining whether an artifact has been generated in a reconstructed tomography image of the heart. Alternatively, the image processor 220 may determine whether a defect has been generated in the reconstructed tomography image, by extracting a point in which a signal level is abruptly changed from the reconstructed tomography image. The image processor 220 may acquire an artifact-containing portion from the object by using various image processing methods.

The image processor 220 may automatically correct, i.e., adjust, a partial period corresponding to a defect-containing region in a tomography image and may automatically correct the portion of the reconstructed image containing the defect, by using image data acquired during the corrected partial period. For example, the image processor 220 may automatically select another defect-free partial period instead of the partial period which has generated a defect, by moving the partial period to another, defect-free location of the same heartbeat period or another heartbeat period.

Referring to FIG. 8B, a discontinuity 826 is generated between the third image section 823 and the second image section 822 due to a volume gap and, thus, a defect has been generated in the third image section 823 of the reconstructed image.

Referring to FIG. 8C, a process of automatically correcting a partial period corresponding to an artifact and automatically correcting an image section having the artifact may be displayed on the screen image 870.

For example, the image processor 220 automatically the partial period P3 corresponding to the third image section 823, which is an artifact-containing image section, into a partial period P3R, and automatically corrects the third image section 823, which is a stair artifact-containing image section, by using image data acquired during the partial period P3R, to avoid an artifact in the final reconstructed image.

The image processor 220 may display this correction process in real time.

For example, a window 880 representing the partial period P3R is marked, and an artifact-corrected third image section 830 obtained by updating the third image section 823 having an artifact is displayed.

When an artifact is generated in a predetermined section of a reconstructed tomography image, the image processor 220 may control at least one of the information provider 460 and the display 230 to output an informing signal that enables a user to visually or acoustically recognize generation of the artifact.

For example, when the information provider 260 includes a speaker (not shown), the information provider 260 may output an announcement broadcast or an alarm sound to inform that the artifact has been generated.

When the information provider 260 includes an alarm lamp (not shown), for example, an LED lamp, the information provider 260 may light on the alarm lamp so that a user may visually recognize generation of the artifact.

Alternatively, the display 230 may display a UI image or a marker informing generation of the defect.

Figure 9A:
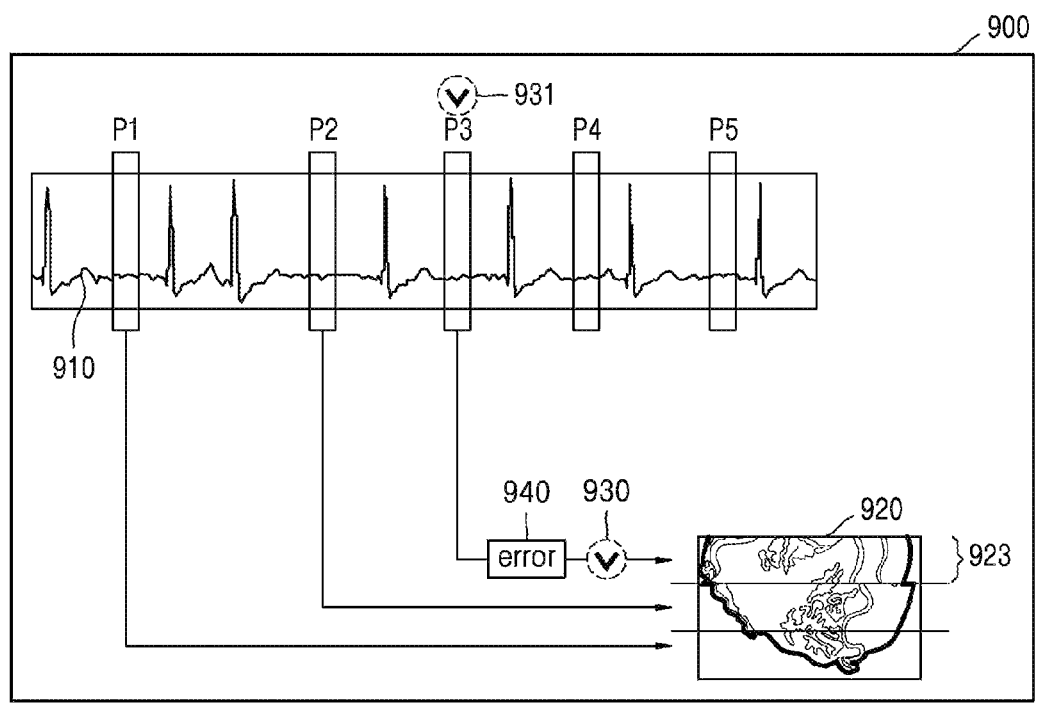
FIG. 9A illustrates another screen image displayed by the tomography apparatus according to an exemplary embodiment.

FIG. 9A illustrates a screen image 900 displayed by the tomography apparatus 200 of FIG. 2. Referring to FIG. 9A, the screen image 900 includes an ECG signal 910 and a reconstructed tomography image 920.

When a defect is generated within the reconstructed tomography image, the image processor 220 may control at least one of a period corresponding to the defect and an image section having the defect in the reconstructed tomography image to be indicated by a marker.

Referring to FIG. 9A, the display 230 may display the screen image 900, in which a partial period P3 corresponding to a defect-containing image section 923 and the defect-containing image section 923 are visually identified by markers 930 and 931.

The image processor 220 may include a message 940 indicating that an error has been generated in the defect-containing image section 923, in the screen image 900.

Figure 9B:
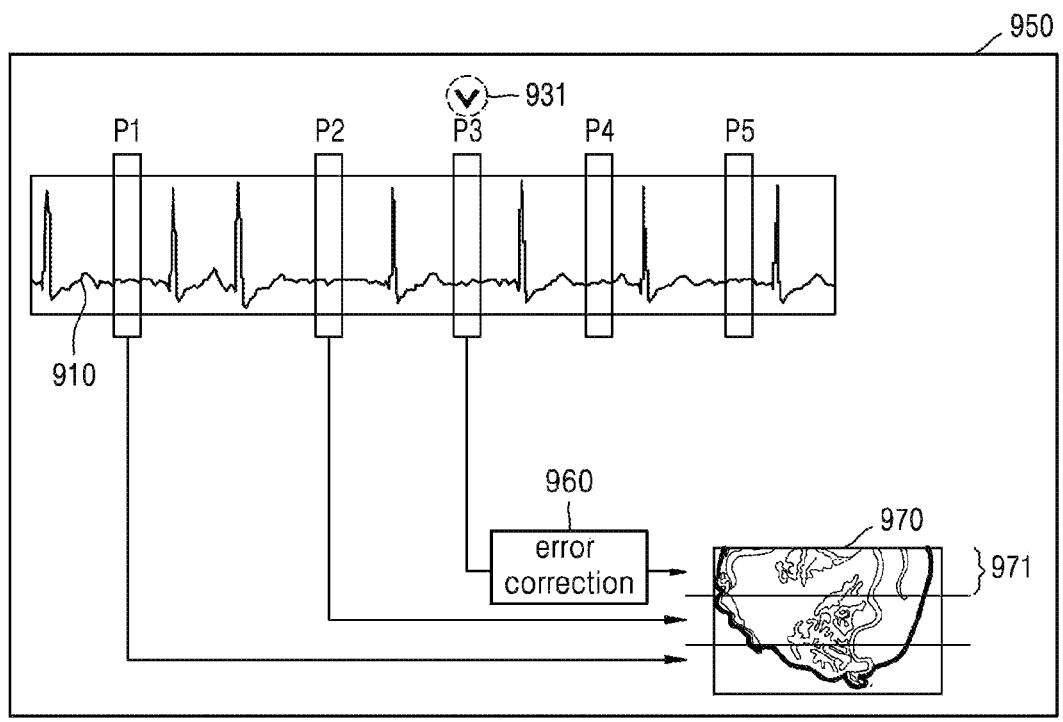
FIG. 9B illustrates another screen image displayed by the tomography apparatus according to an exemplary embodiment.

FIG. 9B illustrates another screen image displayed by the tomography apparatus according to an exemplary embodiment. Components of FIG. 9B that are the same as the components of FIG. 9A are indicated by the same reference numerals or characters, and thus will not be repeated herein.

When the defect-containing image section 923 is generated, the image processor 220 may automatically correct the defect-containing image section 923. For example, when a stair artifact is generated, the image processor 220 may correct an image section 923 containing the stair artifact in order to remove the stair artifact from the image section 923, thereby generating an image section 971 from which the stair artifact has been removed.

Referring to FIG. 9B, the image processor 220 may automatically correct a defect-containing image section (e.g., an image section corresponding to a third period) and may control an defect-corrected tomography image 970 to be displayed on a screen image 950. When the image processor 220 has performed image correction, the image processor 220 may output a message 960 informing that image correction has been performed. The image processor 220 may control a marker 931 indicating the partial period P3 when a defect has been generated to be displayed.

Figure 10:
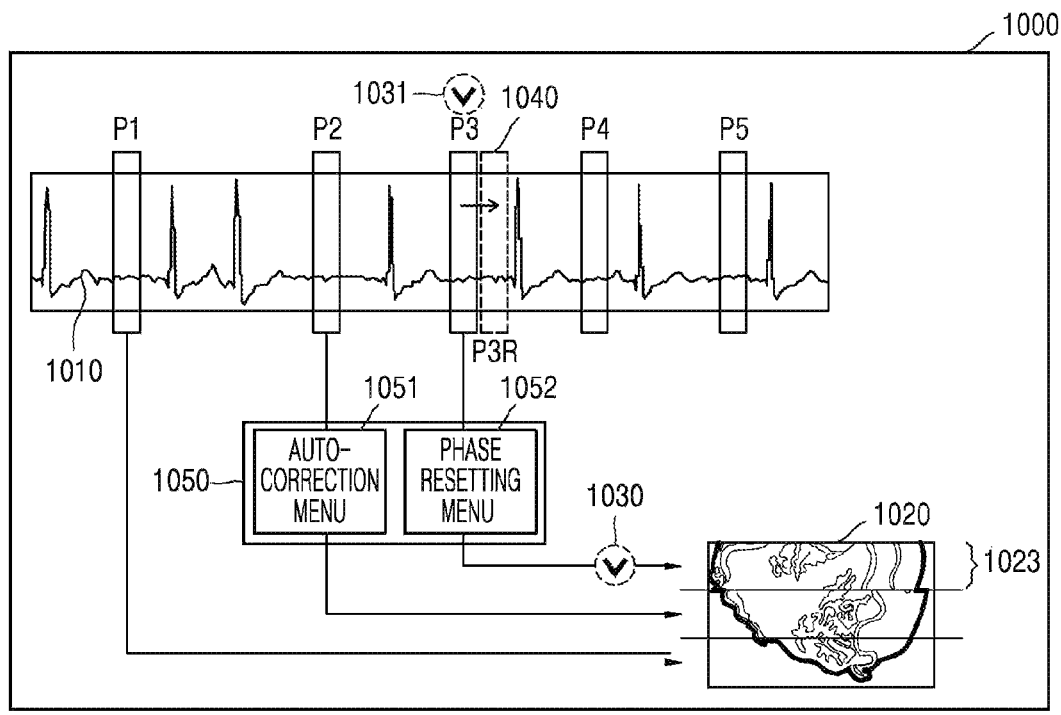
FIG. 10 illustrates another screen image displayed by the tomography apparatus according to an exemplary embodiment.

FIG. 10 illustrates an image 1000 displayed by the tomography apparatus 200 of FIG. 2. Referring to FIG. 10, the screen image 1000 includes an ECG signal 1010, and a reconstructed tomography image 1020.

The image processor 220 may control a menu for re-selecting a partial period corresponding to a defect-containing image section within the reconstructed tomography image to be displayed. The image processor 220 may automatically correct the defect-containing image section by using image data acquired during a re-selected partial period.

Accordingly, the UI unit 240 outputs the menu for re-selecting a partial period corresponding to the defect-containing image section of the reconstructed tomography image, and receives re-selection of the partial period via the menu.

Referring to FIG. 10, the screen image 1000 may include a menu window 1050 for correcting and reconstructing again a defect-containing image section 1023 of the reconstructed tomography image 1020. For example, the menu window 1050 includes at least one of an auto-correction menu 1051 and a phase resetting menu 1052.

In the above-described examples, when the auto-correction menu 1051 is selected, the automatic correction operation according to the period re-selection described above with reference to FIG. 9A is performed. When the auto-correction menu 1051 is selected, the automatic correction operation described above with reference to FIG. 9B may be performed. When the image processor 220 automatically corrects the defect-containing image section 1023, the image processor 220 may enable a user to visually recognize a corrected partial period P3R that has been automatically acquired. Accordingly, the display 230 may display a window 1040 representing the corrected partial period P3R, on the screen image 1000.

The phase re-setting menu 1052 is a menu for re-selecting a partial period corresponding to a defect-containing image section in a reconstructed tomography image. When the phase resetting menu 1052 is selected, a user may manually re-set and input a partial period.

Then, the UI unit 240 may output a UI image suggesting corrected partial periods for phase re-setting to a user and thus may receive a selection of at least one of the corrected partial periods from the user.

Similar to the screen image 900 of FIG. 9A, the screen image 1000 may place at least one of markers 1030 and 1031 to correspond to at least one of the defect-containing image section 1023 and a partial period P3 corresponding to the defect-containing image section 1023.

Figure 11:
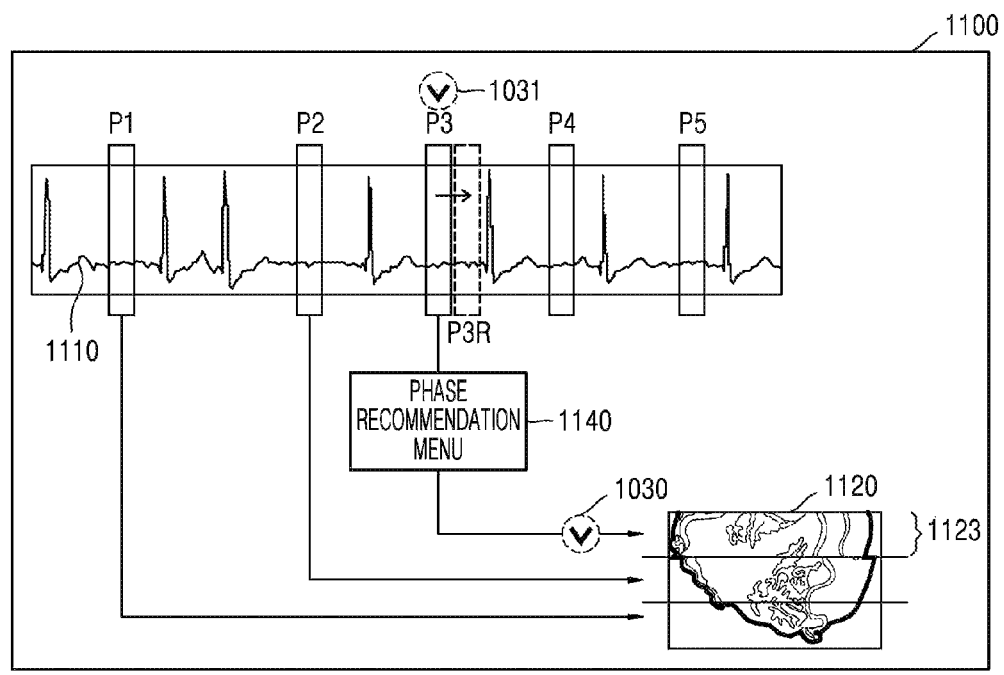
FIG. 11 illustrates another screen image displayed by the tomography apparatus according to an exemplary embodiment.

FIG. 11 illustrates a screen image 1100 displayed by the tomography apparatus 200 of FIG. 2. Referring to FIG. 11, the screen image 1100 includes an ECG signal 1110, and a reconstructed tomography image 1120.

When a defect is generated in a reconstructed tomography image, the image processor 220 may extract from the heartbeat period one or more partial periods that prevents generation of a defect within the reconstructed tomography image, and may control an UI image for recommending the extracted partial period to a user to be output. For example, the recommended partial period may include a defect-free portion of the same partial period or another defect-free partial period included in the same heartbeat period or in another heartbeat period. Accordingly, the display 230 may display the UI image for a phase portion recommendation.

Referring to FIG. 11, the screen image 1100, which is a UI image for phase recommendation, may include a phase recommendation menu 1140 for correcting a partial period P3 corresponding to a defect-containing image section 1123 of the reconstructed tomography image 1120.

When the phase recommendation menu 1140 is selected, as illustrated in FIG. 11, at least one recommended partial period (for example, a partial period P3R) may be displayed, and a user may select at least one of the recommended partial periods via the UI unit 240. Although only the single partial period P3R is recommended in FIG. 11, a plurality of partial periods may be recommended.

For example, when image data is acquired by performing a tomography scan according to the axial scanning method, additional data is acquired in the first and second padding sections 471 and 475, which are time sections before and after a data section that is to be used, as described above with reference to FIG. 4B. When the partial period of FIG. 11 corresponds to a time section during which the first data amount 461 is acquired, the recommended partial period P3R may be a time section between the time point t41 and the time point t42. For example, the recommended partial period P3R may be a time section 481 including a portion of the first padding section 471 or may be a time section 482 including a portion of the second padding section 475.

Depending on which section of the image data 460 is used to perform image reconstruction, an artifact may have different aspects due to a change in a heartbeat rate. Accordingly, the image processor 220 may provide a time section when a small artifact is generated, as the recommended partial period P3R.

When image data is acquired by performing a tomography scan according to the helical scanning method, pieces of image data are acquired in consecutive time sections, as described above with reference to FIG. 3. Thus, a time section when a small artifact is generated may be selected or extracted from the predetermined time period from t=0 to t=end and may be provided as the recommended partial period P3R.

Then, the image processor 220 may reconstruct again a tomography image including the defect-containing image section 1123 by using image data acquired during the selected at least one partial period.

Alternatively, after a tomography image representing the entire object is reconstructed, the image processor 220 may detect a defect-containing image section from the reconstructed CT image and reconstruct again the defect-containing image section as described in detail below with reference to FIGS. 12 and 13.

Figure 12:
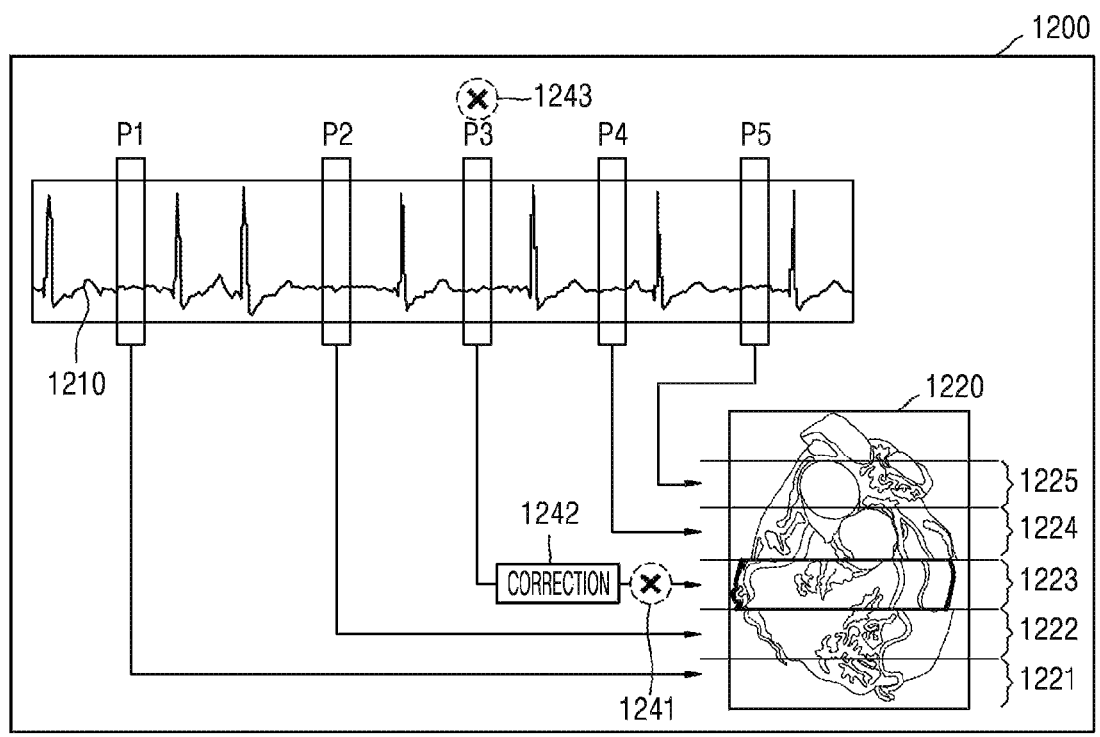
FIG. 12 illustrates another screen image displayed by the tomography apparatus according to an exemplary embodiment.

FIG. 12 illustrates a screen image 1200 displayed by the tomography apparatus 200 of FIG. 2. Referring to FIG. 12, the screen image 1200 includes an ECG signal 1210, and a reconstructed entire tomography image 1220.

Referring to FIG. 12, the image processor 220 reconstructs a first image section 1221 by using image data acquired during a partial period P1, reconstructs a second image section 1222 by using image data acquired during a partial period P2, reconstructs a third image section 1223 by using image data acquired during a partial period P3, a fourth image section 1224 by using image data acquired during a partial period P4 and reconstructs a fifth image section 1225 by using image data acquired during a partial period P5. Then, the image processor 220 displays the reconstructed entire tomography image 1220. The reconstructed entire tomography image 1220 is an entire tomography image representing the entire object.

The image processor 220 may extract the third image section 1223 having a defect from the reconstructed entire tomography image 1220 and may place at least one of markers 1241 and 1243 on at least one of the extracted third image section 1223 having the defect and a partial period corresponding to the extracted third image section 1223 having the defect.

The image processor 220 may control to display an informing message 1242 informing that the third image section 1223 having the defect needs to be corrected.

Figure 13:
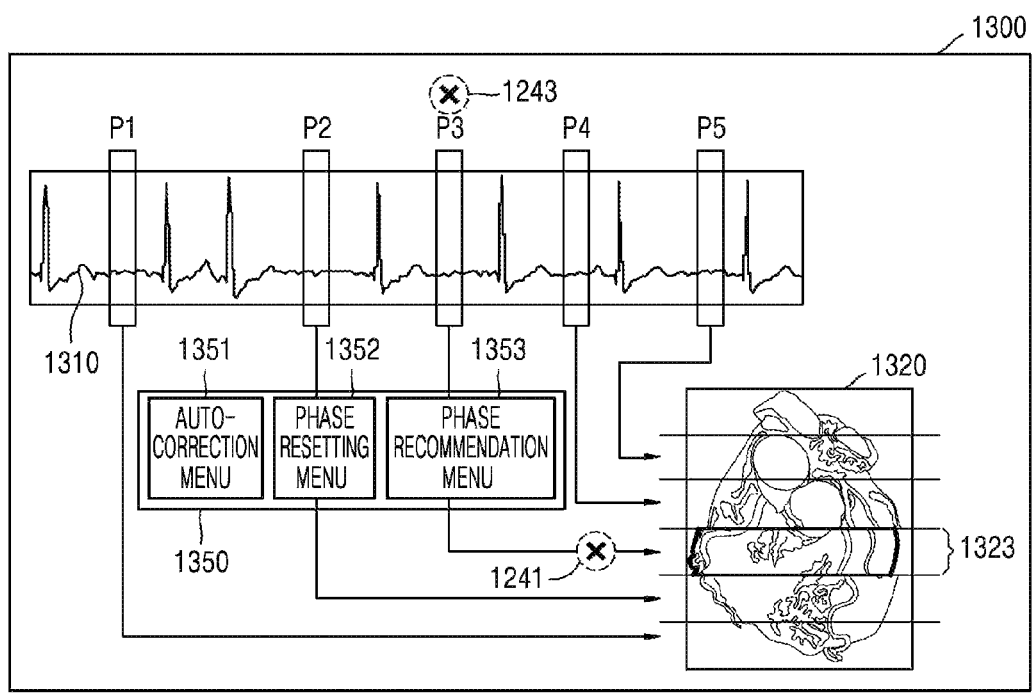
FIG. 13 illustrates another screen image displayed by the tomography apparatus according to an exemplary embodiment.

FIG. 13 illustrates a screen image 1300 displayed by the tomography apparatus 200 of FIG. 2. Referring to FIG. 13, the screen image 1300 includes an ECG signal 1310, and a reconstructed entire tomography image 1320.

The image processor 220 may control a menu window 1350 for correcting a defect-containing image section 1323, to be output.

The menu window 1350 includes at least one of an auto-correction menu 1351, a phase resetting menu 1352, and a phase recommendation menu 1353. The auto-correction menu 1351, the phase resetting menu 1352, and the phase recommendation menu 1353 correspond to the auto-correction menu 1051, the phase resetting menu 1052, and the phase recommendation menu 1140, respectively, which are described above, and thus a detailed description thereof will be omitted.

In a related art tomography image reconstruction, only after an entire tomography image representing the entire object is reconstructed, an image defect is determined. Thus, even when a defect is generated in only a portion of the entire tomography image, the entire tomography image needs to be acquired again, to generate a defect-free tomography image. In addition, the time for a patient to be exposed to radiation is increased due to re-scanning, negatively effecting the patient's health.

As described above, the tomography apparatus 200 according to an exemplary embodiment display partial periods included in a heartbeat period and reconstructed image sections corresponding to the partial periods in association with each other. Thus, a user may immediately ascertain whether a defect has been generated, and may also ascertain a partial period corresponding to a defect-containing image section in real time. Accordingly, before the entire tomography image representing the entire object is reconstructed, the user may take measures to remove the defect, thereby more quickly acquiring a defect-free tomography image.

In addition, by checking the mapped partial periods in real time, when a defect is generated in an image section, only a partial period corresponding to the defect-containing image section may be corrected, and thus the defect-containing image section may be reconstructed again. Accordingly, when a defect is generated, the entire tomography image is not reconstructed again but is partially reconstructed again, leading to a reduction in the time taken to acquire a defect-free tomography image.

Moreover, the image processor 220 according to an exemplary embodiment reconstructs a tomography image by using a plurality of pieces of image data that are acquired during a plurality of partial periods included in the heartbeat period. When a defect is generated in the reconstructed tomography image, the image processor 220 may automatically reconstruct again a defect-containing image section of the reconstructed tomography image by using corrected image data acquired during a corrected partial period. The display 230 may display an image including a reconstructed tomography image, update a defect-containing image section of the reconstructed tomography image with a reconstructed again image section in real time, and display a result of the updating.

Figure 14A:
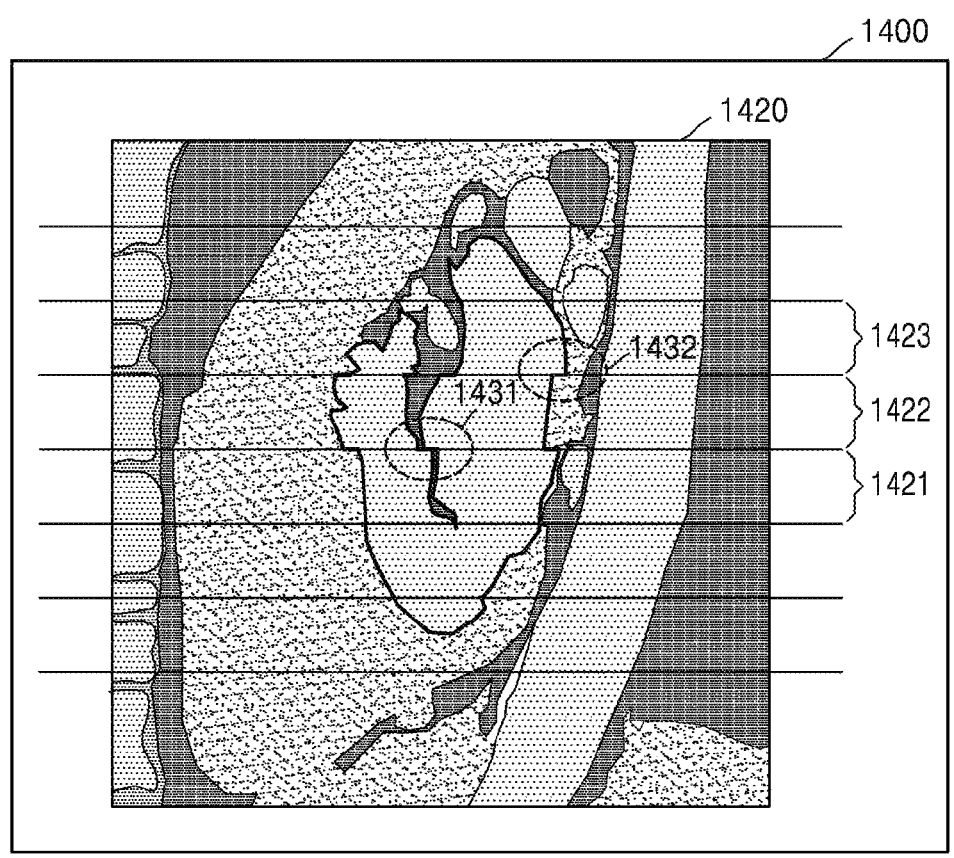
FIGS. 14A and 14B illustrate other screen images displayed by the tomography apparatus according to an exemplary embodiment.
Figure 14B:
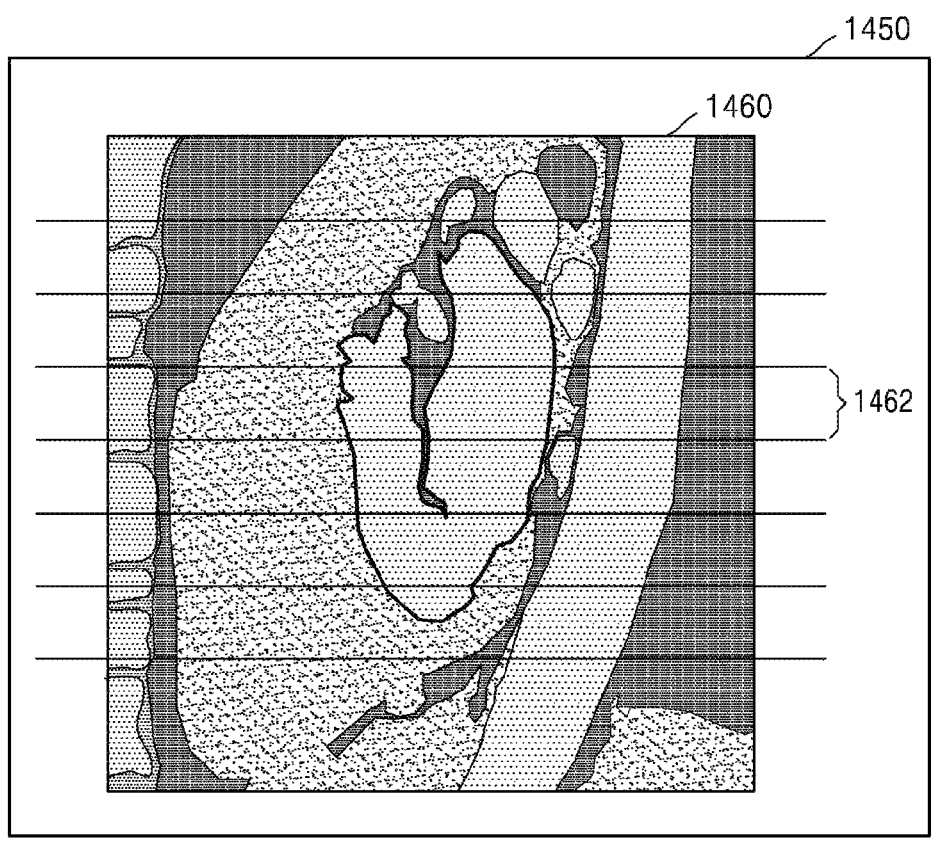

FIGS. 14A and 14B illustrate screen images 1400 and 1450 displayed by the tomography apparatus 200 of FIG. 2. Referring to FIG. 14A, the display 230 displays the screen image 1400, which includes a reconstructed tomography image 1420 having a defect generated in a certain section thereof. Referring to FIG. 14B, the display 230 displays the screen image 1450, which includes a tomography image 1460 obtained by updating the tomography image 1420 in real time.

Referring to FIG. 14A, in the reconstructed tomography image 1420, a defect is generated in an image section 1422 from among a plurality of image sections 1421, 1422, and 1423 reconstructed in correspondence to a plurality of partial periods. The image section 1422 will now be referred to as a defective image section 1422.

Due to a volume gap generated in the defective image section 1422, discontinuities 1431 and 1432 are generated within the reconstructed tomography image 1420.

Referring to FIG. 14B, the image processor 220 may generate a reconstructed again image section 1462 by automatically reconstructing again the defective image section 1422 by using corrected image data acquired during a corrected partial period. The display 430 may display the screen image 1450 including the tomography image 1460 obtained by updating the defective image section 1422 in real time.

Accordingly, the tomography image 1460 from which the discontinuities 1431 and 1432 on the screen image 1400 have been removed is displayed on the screen image 1450.

For example, when a defect is generated in the reconstructed tomography image 1420, the image processor 220 may acquire, from the heartbeat period, position information of a corrected partial period that prevents generation of a defect. Based on the position information of the corrected partial period, the image processor 220 may reconstruct again the defective image section 1422 by using corrected image data acquired during the corrected partial period.

The position information of the corrected partial period may be acquired by the image processor 220 analyzing an ECG signal.

Alternatively, the position information of the corrected partial period may be received from a user via the UI unit 240. When the position information of the corrected partial period is received from an external source, the UI unit 240 may output a menu window (not shown) for recommending at least one corrected partial period that prevents generation of a defect, and may receive selection of at least one corrected partial period from the user via the menu window. When the corrected partial period is selected and received, the image processor 220 may reconstruct again the defective image section 1422 by using corrected image data acquired during the selected at least one corrected partial period to generate an updated tomography image. Accordingly, the tomography image 1460 includes the reconstruct again image section 1462 instead of the defective image section 1422.

Figure 15:
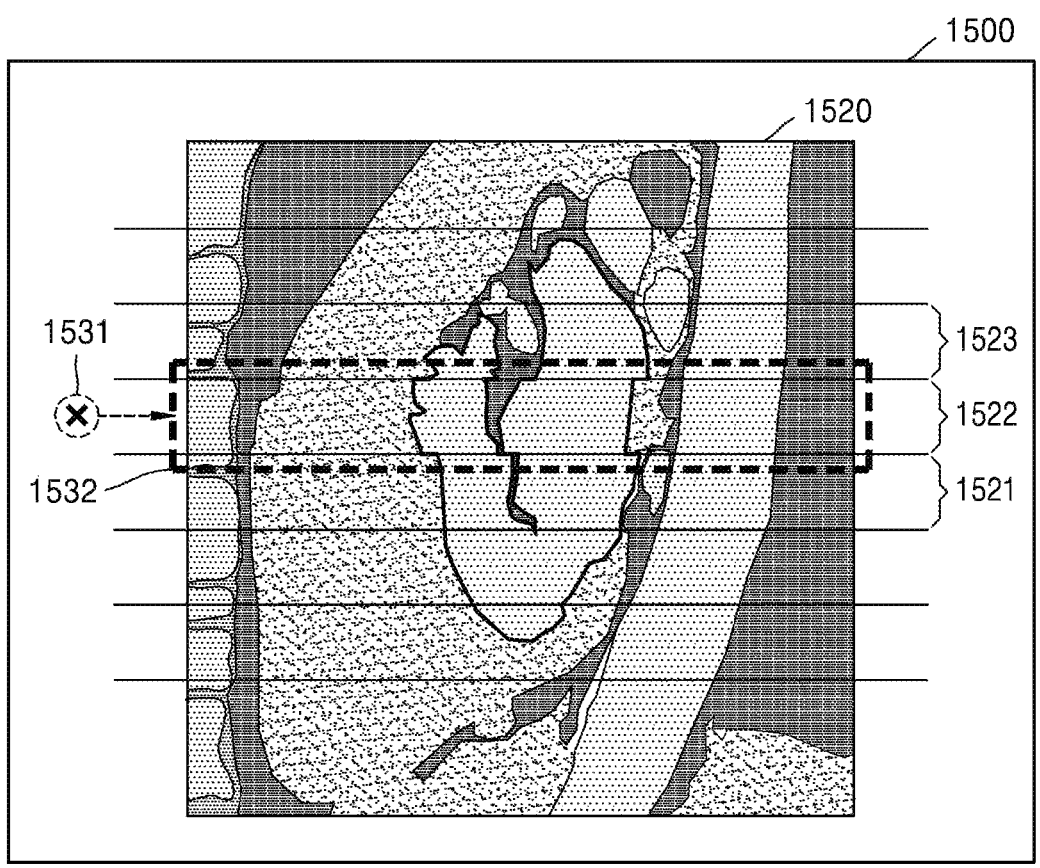
FIG. 15 illustrates another screen image displayed by the tomography apparatus according to an exemplary embodiment.

FIG. 15 illustrates a screen image 1500 displayed by the tomography apparatus 200 of FIG. 2. Referring to FIG. 15, the display 230 displays the screen image 1500, which includes a tomography image 1520 having a defect generated in a certain section thereof.

Referring to FIG. 15, a defect-containing image section 1522 and defect-free image sections 1521 and 1523 may be distinguished from each other and displayed on the screen image 1500. For example, the defect-containing image section 1522 may be indicated by a highlight 1532 on the screen image 1500. A marker 1531 informing a defect may also be placed adjacent to the defect-containing image section 1522 on the screen image 1500.

Figure 16:
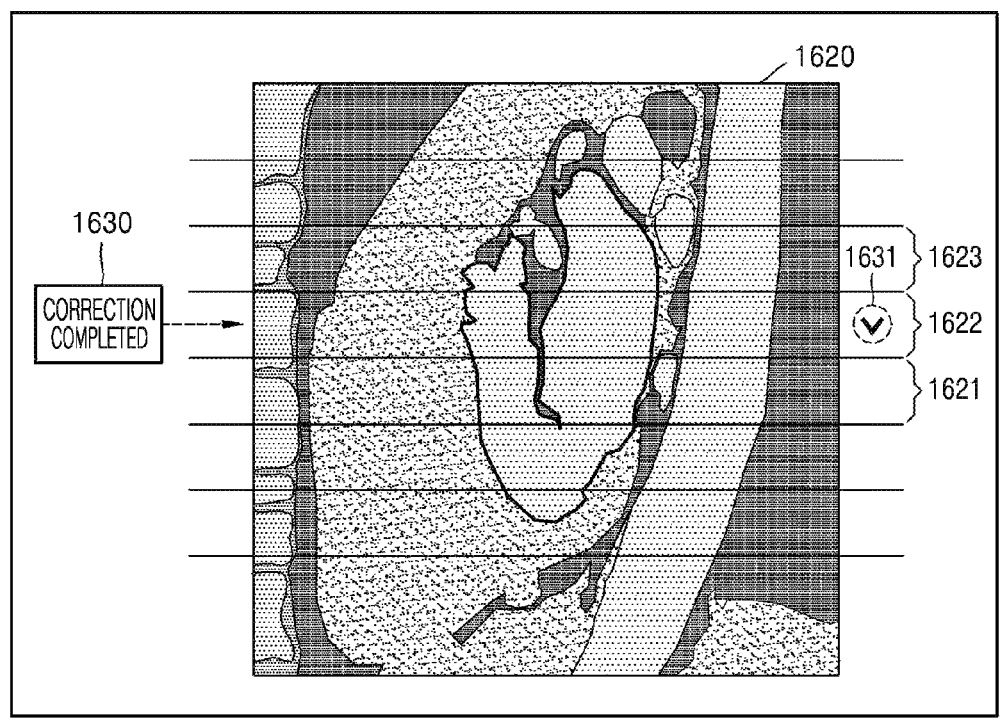
FIG. 16 illustrates another screen image displayed by the tomography apparatus according to an exemplary embodiment.

FIG. 16 illustrates a screen image 1600 displayed by the tomography apparatus 200 of FIG. 2. Referring to FIG. 16, the display 230 displays the screen image 1600, which includes a real-time updated tomography image 1620 obtained by reconstructing again the defect-containing image section 1522 of FIG. 15.

Referring to FIG. 16, an updated image section 1622 and not-updated image sections 1621 and 1623 may be distinguished from each other and displayed on the screen image 1600.

For example, a message 1630 informing that the updated image section 1622 has been obtained may be displayed. As described above with reference to FIG. 15, the updated image section 1622 may be indicated by a highlight (not shown). As described above with reference to FIG. 15, a marker 1631 informing that the updated image section 1622 has been obtained may also be displayed near the updated image section 1622.

Figure 17:
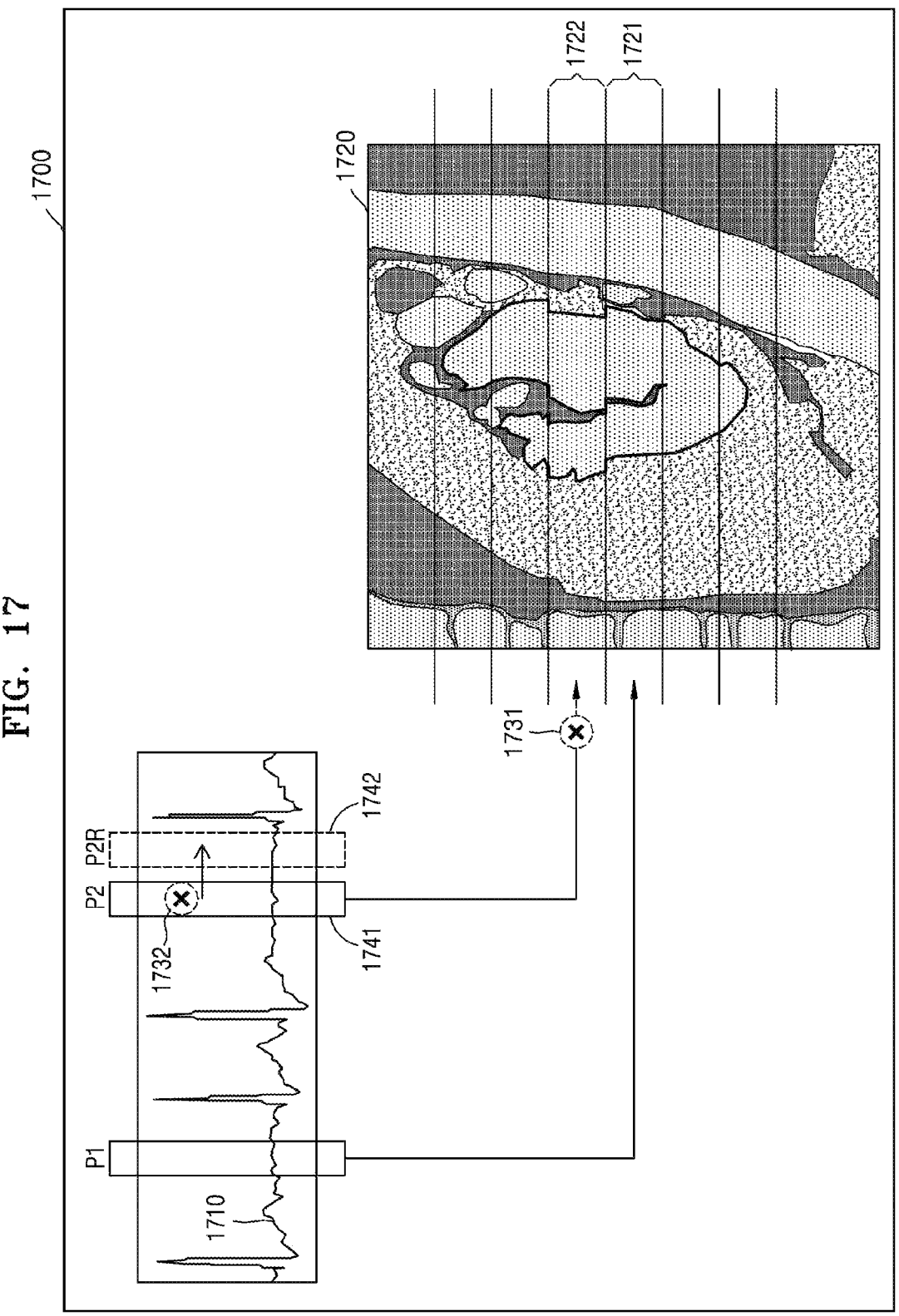
FIG. 17 illustrates another screen image displayed by the tomography apparatus according to an exemplary embodiment.

FIG. 17 illustrates a screen image 1700 displayed by the tomography apparatus 200 of FIG. 2.

Referring to FIG. 17, the screen image 1700 displayed by the display 230 may further include an ECG signal 1710 representing a heartbeat period.

For example, the screen image 1700, as illustrated in FIGS. 7-13, may display an image section corresponding to at least one of a plurality of partial periods included in the heartbeat period such that the image section is associated with the partial period.

Referring to FIG. 17, an image section 1721 has been reconstructed using image data acquired during a partial period P1 and an image section 1722 has been reconstructed using image data acquired during a partial period P2.

When a defect is generated in the image section 1722 of a reconstructed tomography image 1720, markers 1731 and 1732 representing defects may be displayed on at least one of the defect-containing image section 1722 and a partial period P2 corresponding to the defect-containing image section 1722.

When the defect-containing image section 1722 is automatically corrected using a corrected partial period P2R, the corrected partial period P2R may indicated by a window 1742 and displayed. For example, as illustrated in FIG. 17, an arrow indicating a change of a window 1741 representing the partial period P2 to the window 1742 representing the corrected partial period P2R may be displayed on the screen image 1700 to represent that the partial period P2, which is used to reconstruct the image section 1722, has been changed to the corrected partial period P2R.

As described above, when a defect is generated in an image section of a tomography image, the tomography apparatus 200 according to an exemplary embodiment reconstructs again the defect-containing image section by using corrected image data acquired during a corrected partial period and obtains and displays a real-time updated tomography image including a reconstructed again image section corresponding to a result of the re-reconstruction.

Accordingly, the tomography apparatus 200 may correct only a partial period corresponding to the defect-containing image section and reconstruct again the defect-containing image section. Therefore, when a defect is generated, the entire tomography image is not reconstructed again but is partially reconstructed again, leading to a reduction in the time taken to acquire a defect-free tomography image.

Figure 18:
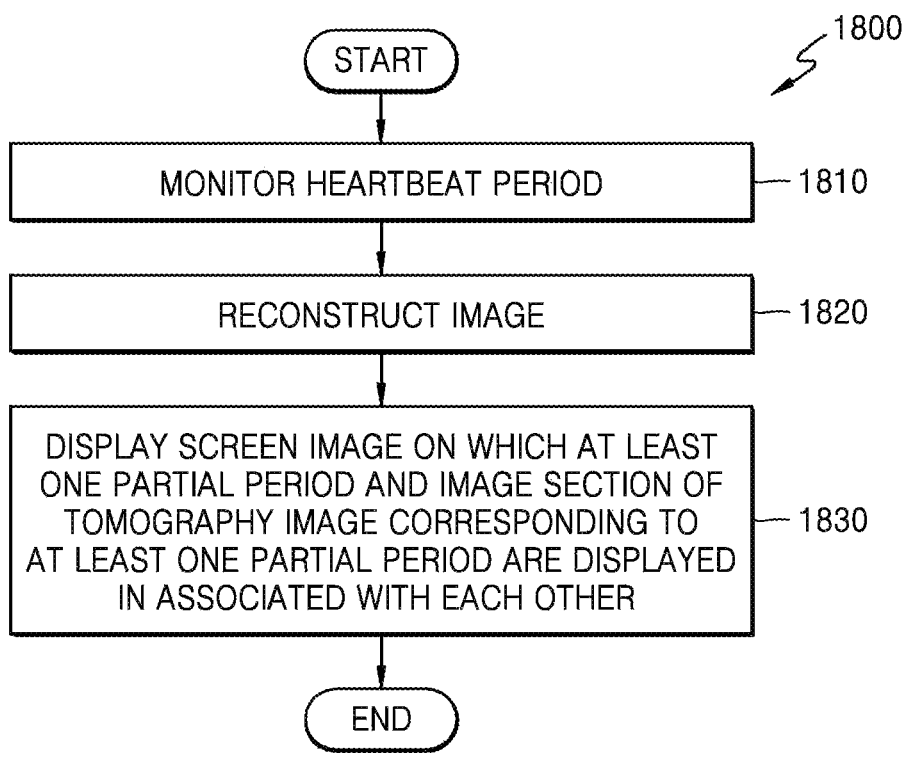
FIG. 18 is a flowchart of a tomography image displaying method according to an exemplary embodiment.

FIG. 18 is a flowchart of a tomography image displaying method 1800 according to an exemplary embodiment. The tomography image displaying method 1800 may be performed by the tomography apparatus 200 of FIG. 2. Operations of the tomography image displaying method 1800 include the same technical features as those of the above-described operations of the tomography apparatus 200 and a repeated description is omitted.

Referring to FIG. 18, a heartbeat period is monitored, in operation 1810.

In operation 1820, a tomography image is reconstructed using a plurality of pieces of image data that are acquired during a plurality of partial periods included in the heartbeat period monitored in operation 1810.

In operation 1830, a screen image including the tomography image and information representing the heartbeat period is displayed.

For example, the screen image displayed in operation 1830 may correspond to the screen images illustrated in FIGS. 7-13.

When a defect is generated in the tomography image included in the image displayed in operation 1830, the tomography image displaying method 1800 may further include an operation (not shown) of extracting, from the heartbeat period, at least one partial period that prevents a defect from being generated in the tomography image and an operation (not shown) of outputting a UI image for recommending the extracted partial period to a user. For example, the UI image 1100 or 1300 of FIG. 11 or 13 for recommending at least one extracted partial period to a user may be displayed.

When a defect is generated in the tomography image, the tomography image displaying method 1800 may further include an operation (not shown) of automatically correcting a partial period corresponding to a defect-containing image section of the tomography image and automatically correcting the defect-containing image section by using image data acquired during the corrected partial period.

Figure 19:
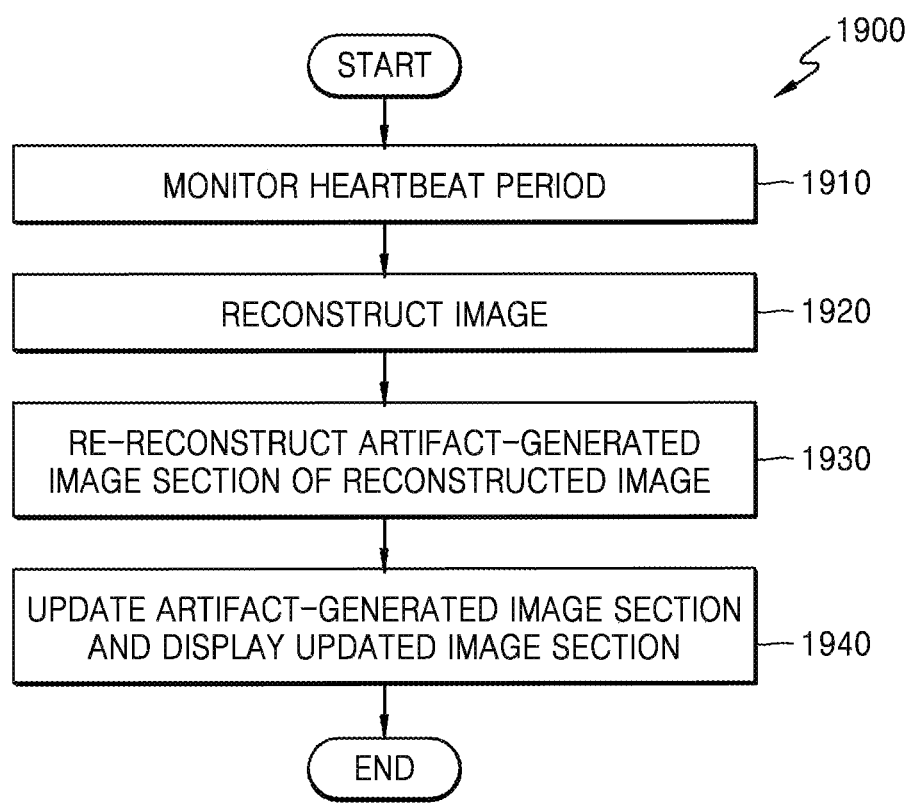
FIG. 19 is a flowchart of a method a tomography image displaying method according to another exemplary embodiment.

FIG. 19 is a flowchart of a tomography image displaying method 1900 according to another exemplary embodiment. The tomography image displaying method 1900 may be performed by the tomography apparatus 200 of FIG. 2. Operations of the tomography image displaying method 1900 include the same technical features as those of the above-described operations of the tomography apparatus 200 and a repeated description is omitted.

Referring to FIG. 19, a heartbeat period is monitored, in operation 1910.

In operation 1920, a tomography image is reconstructed using a plurality of pieces of image data that are acquired during a plurality of partial periods included in the heartbeat period monitored in operation 1910.

When a defect is generated in the tomography image reconstructed in operation 1920, a defect-containing image section of the reconstructed tomography image is automatically reconstructed again using corrected image data acquired during a corrected partial period, in operation 1930.

A screen image including the tomography image reconstructed in operation 1920 is displayed. In operation 1940, the defect-containing image section is updated using a reconstructed again image section obtained in operation 1930, and an update is then displayed.

FIG. 20A illustrates a screen image 2000 displayed by the display 230 under the control of the image processor 220.

The image processor 220 may reconstruct a tomography image corresponding to a predetermined region 2011 of a medical image 2010 including an object, which is a heart, by using a plurality of pieces of image data that are acquired during a plurality of partial periods included in a heartbeat period.

Referring to FIG. 20A, a tomography image representing an object included in a region of interest (ROI), which is the predetermined region 2011, may be reconstructed. The medical image 2010 may be a scout image obtained by imaging the entire object, and an X-ray image, an ultrasonic image, an MRI image, a 3D tomography image, or the like may be used as the medical image 2010. FIG. 20A illustrates a case where the object is a chest and the medical image 2010 is an X-ray scout image.

The predetermined region 2011 may be set by a user via the UI unit 240. Alternatively, the image processor 220 may automatically extract and set the predetermined region 2011.

A tomography image corresponding to the set predetermined region 2011 is reconstructed. For example, as described above with reference to FIGS. 7-17, the tomography image representing the object is reconstructed in units of sections by using image data acquired during each partial period included in the heartbeat period. Referring to FIG. 20A, pieces of image data acquired during a plurality of partial periods P1, P2, P3, and P4 are used to reconstruct the tomography image corresponding to the predetermined region 2011.

For example, referring to FIG. 20A, the image processor 220 reconstructs a first image section 2071 by using image data acquired during the partial period P1, reconstructs a second image section 2072 by using image data acquired during the partial period P2, reconstructs a third image section 2073 by using image data acquired during the partial period P3, and reconstructs a fourth image section 2074 by using image data acquired during the partial period P4.

The reconstructed tomography image may be a transverse cross-sectional tomography image.

The display 230 may display the screen image 2000, which includes the medical image 2010 and information 2031 representing a heartbeat period 2030 and on which the plurality of partial periods P1, P2, P3, and P4 and the first, second, third, and fourth image sections 2071, 2072, 2073, and 2074 of the predetermined region 2011 are shown in association with each other. In other words, the screen image 2000 may include an area 2001 on which the medical image 2010 is displayed, and an area 2005 on which the information 2031 representing the heartbeat period 2030 is displayed.

For example, in FIG. 20A, the association shown may be a color association in which each section of the predetermined region 2011 and a partial period corresponding to the section are expressed in the same color. For example, the partial period P1 of the ECG signal 2030 and the first image section 2071 of the medical image 2010 may be expressed in a same color 2032, the partial period P2 of the ECG signal 2030 and the second image section 2072 of the medical image 2010 may be expressed in a same color 2033, the partial period P3 of the ECG signal 2030 and the third image section 2073 of the medical image 2010 may be expressed in a same color 2034, and the partial period P4 of the ECG signal 2030 and the fourth image section 2074 of the medical image 2010 may be expressed in a same color 2035. The association between at least one partial period and at least one image section may be displayed in various other methods of connecting each section of the predetermined region 2011 to a period of the ECG signal 2030 that corresponds to the section. As another example, period information 2062 may be added to each section of the predetermined region 2011.

The screen image 2000 may further display at least one partial image 2020 of a tomography image reconstructed by the image processor 220.

The partial image 2020 may be a transverse cross-sectional tomography image as described above.

An image section and/or a partial period associated with a current tomography image reconstruction operation may be displayed on the screen image 2000. For example, when image reconstruction is performed with respect to the second image section 2072, at least one of the second image section 2072 and the partial period P2 may be indicated by at least one of highlights 2050 and 2040 as illustrated in FIG. 20. Accordingly, a user may easily recognize an image section that is currently being reconstructed.

The partial image 2020 may be an image included in the image section that is being currently reconstructed.

The screen image 2000 may show the partial image 2020 and a section of the predetermined region 2011 that corresponds to the partial image 2020 such that they are associated with each other. For example, an additional marker indicating the image section that is being currently reconstructed may be displayed on the partial image 2020. For example, since the image section that is currently being reconstructed corresponds to the partial period P2, a 'P2' marker 2060 may be additionally displayed on the partial image 2020.

FIG. 20B is a view for explaining a scout image.

The medical image 2010 included in the screen image 2000 of FIG. 20A may be an image including any of various views. In other words, the medical image 2010 may be an image including a view from which the location of the predetermined region 2011 can be ascertained.

For example, the medical image 2010 included in the screen image 2000 may be a scout image 2080 representing an anteroposterior view, as illustrated in (a) of FIG. 20B. Alternatively, the medical image 2010 included in the screen image 2000 may be a scout image 2085 representing a lateral view, as illustrated in (b) of FIG. 20B.

Figure 20C:
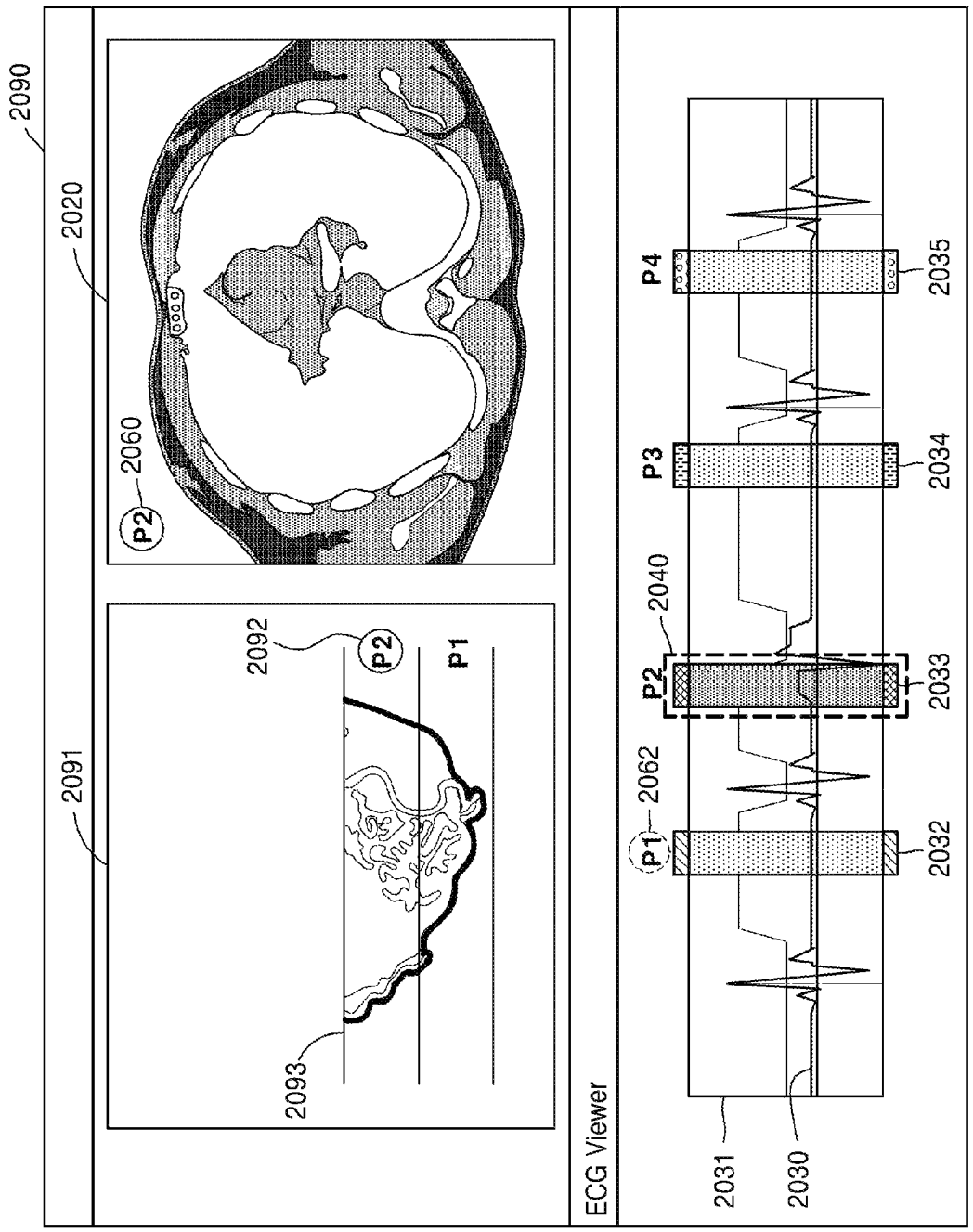
FIG. 20C illustrates another screen image displayed by the tomography apparatus according to an exemplary embodiment.

FIG. 20C illustrates another screen image displayed by the tomography apparatus according to an exemplary embodiment. Components of FIG. 20C that are the same as the components of FIG. 20A are indicated by the same reference numerals or characters, and thus will not be repeated herein.

Referring to FIG. 20C, a screen image 2090 may correspond to the screen image 2000 of FIG. 20A.

The screen image 2090 may include a reconstructed tomography image 2091 instead of the medical image 2010. The reconstructed tomography image 2091 may be a tomography image that is updated in real time according to an image reconstruction operation and includes an image section reconstructed up to a current time. The screen image 2090 may display the reconstructed tomography image 2091 and a partial period of a heartbeat period such that the reconstructed tomography image 2091 is associated with the partial period. For example, a marker (e.g., a 'P2' marker 2092) indicating a partial period may be displayed for each image section of the reconstructed tomography image 2091. To distinguish a partial period used in reconstructing the reconstructed tomography image 2091 from a partial period adjacent thereto, a line 2093 may be displayed as illustrated in FIG. 20C.

FIG. 21 illustrates a screen image 2100 displayed by the display 230 under the control of the image processor 220. The screen image 2100 of FIG. 21 corresponds to the screen image 2000 of FIG. 20A, and repeated images and reference characters in FIG. 21 are the same as those in FIG. 20A. Thus, a repeated description thereof will be omitted.

Referring to FIG. 21, a portion of the predetermined region 2011 that is being currently reconstructed may be marked on the screen image 2100. The partial image 2020 may be a currently reconstructed cross-sectional image.

For example, during tomography image reconstruction, a cross-sectional image is reconstructed at regular intervals. For example, after a cross-sectional tomography image of a cross-section 2110 is reconstructed, a cross-sectional tomography image of a cross-section 2120 may be reconstructed. The screen image 2100 may display a cross-sectional tomography image of the cross-section 2120 currently being reconstructed, as the partial image 2020. Accordingly, as reconstruction proceeds, the partial image 2020 may be updated in real time and displayed. As illustrated in FIG. 21, a point of the predetermined region 2011 that is being reconstructed and a direction in which the predetermined region 2011 is reconstructed are indicated by an arrow 2150 so that a user may easily recognize the point that is being reconstructed. An updated tomography image and a section of the predetermined region 2011 that corresponds to the updated tomography image may be displayed in association with each other on the screen image 2100. An updated tomography image and a partial period of the heartbeat period that corresponds to the updated tomography image may be displayed in association with each other on the screen image 2100.

Figure 22:
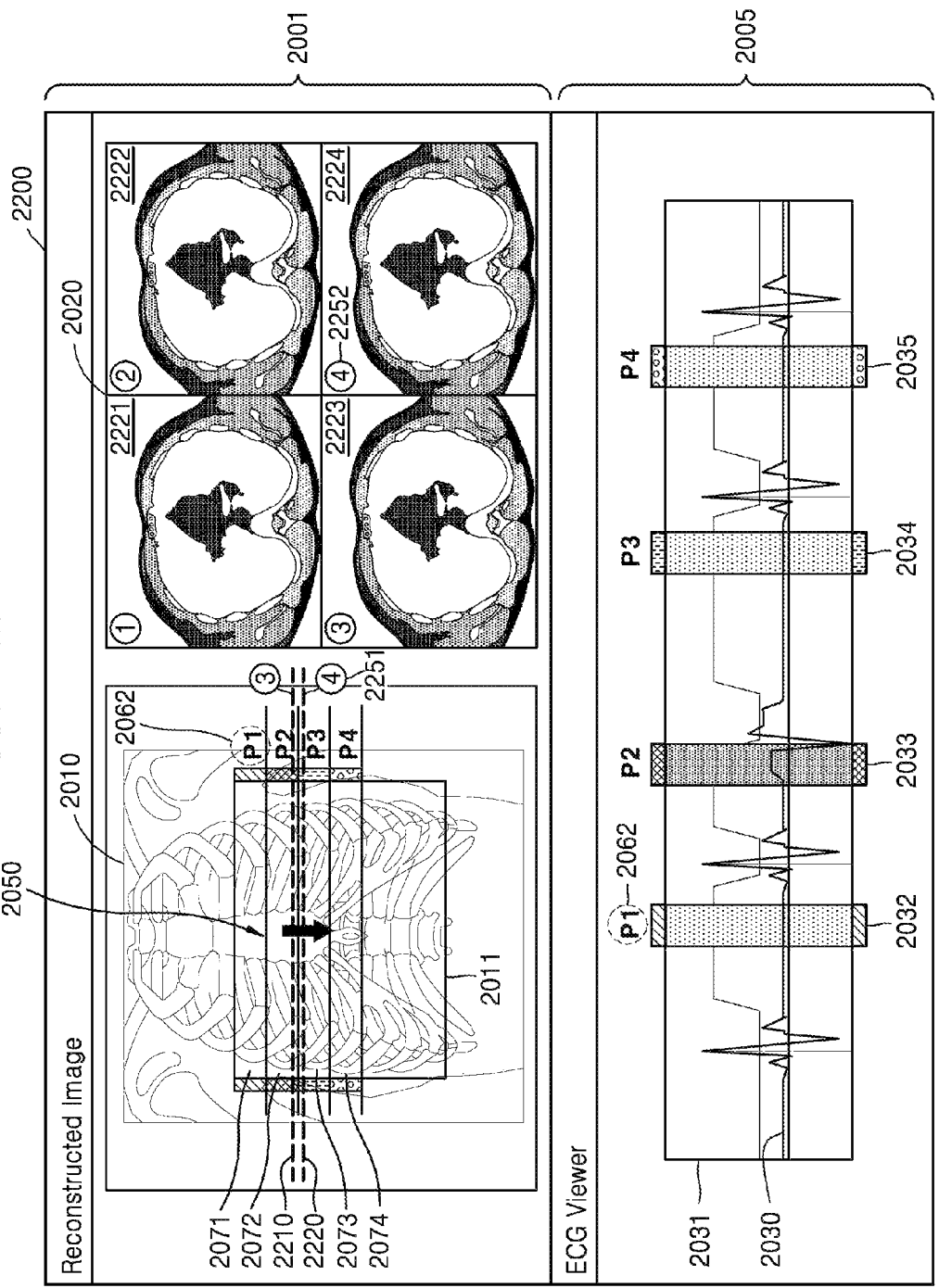
FIG. 22 illustrates another screen image displayed by the tomography apparatus according to an exemplary embodiment.

FIG. 22 illustrates a screen image 2200 displayed by the tomography apparatus 200 of FIG. 2. The screen image 2200 is a screen image displayed by the display 230 under the control of the image processor 220. The screen image 2200 of FIG. 22 corresponds to the screen image 2100 of FIG. 21, and images and reference characters that are the same as those in FIG. 21 are repeated in FIG. 22. Thus, a repeated description thereof will be omitted.

Referring to FIG. 22, as reconstruction of a tomography image included in the predetermined region 2011 proceeds, a currently reconstructed cross-sectional tomography image and at least one previously reconstructed cross-sectional tomography image may be displayed together on the screen image 2200. For example, the currently reconstructed cross-sectional tomography image 2224 and at least one of cross-sectional tomography images 2221, 2222, and 2223 may be displayed on an area 2020.

As illustrated in the discontinuity 826 of FIG. 8, the probability of generation of a stair artifact in an image is high in a section where a partial period changes. Accordingly, a reconstructed tomography image corresponding to a section of the predetermined region 2011 in which a stair artifact is highly likely to be generated may be displayed on the area 2020.

For example, a plurality of cross-sectional tomography images corresponding to a region between the second and third image sections 2072 and 2073 where a partial period changes may be displayed on the area 2020. A cross-section within the predetermined region 2011 and a cross-sectional tomography image corresponding to the cross-section may be displayed in association with each other. For example, markers 2251 and 2252 indicating the same cross-section may be additionally displayed on the cross-section within the predetermined region 2011 and a cross-sectional tomography image 2224, respectively.

Figure 23:
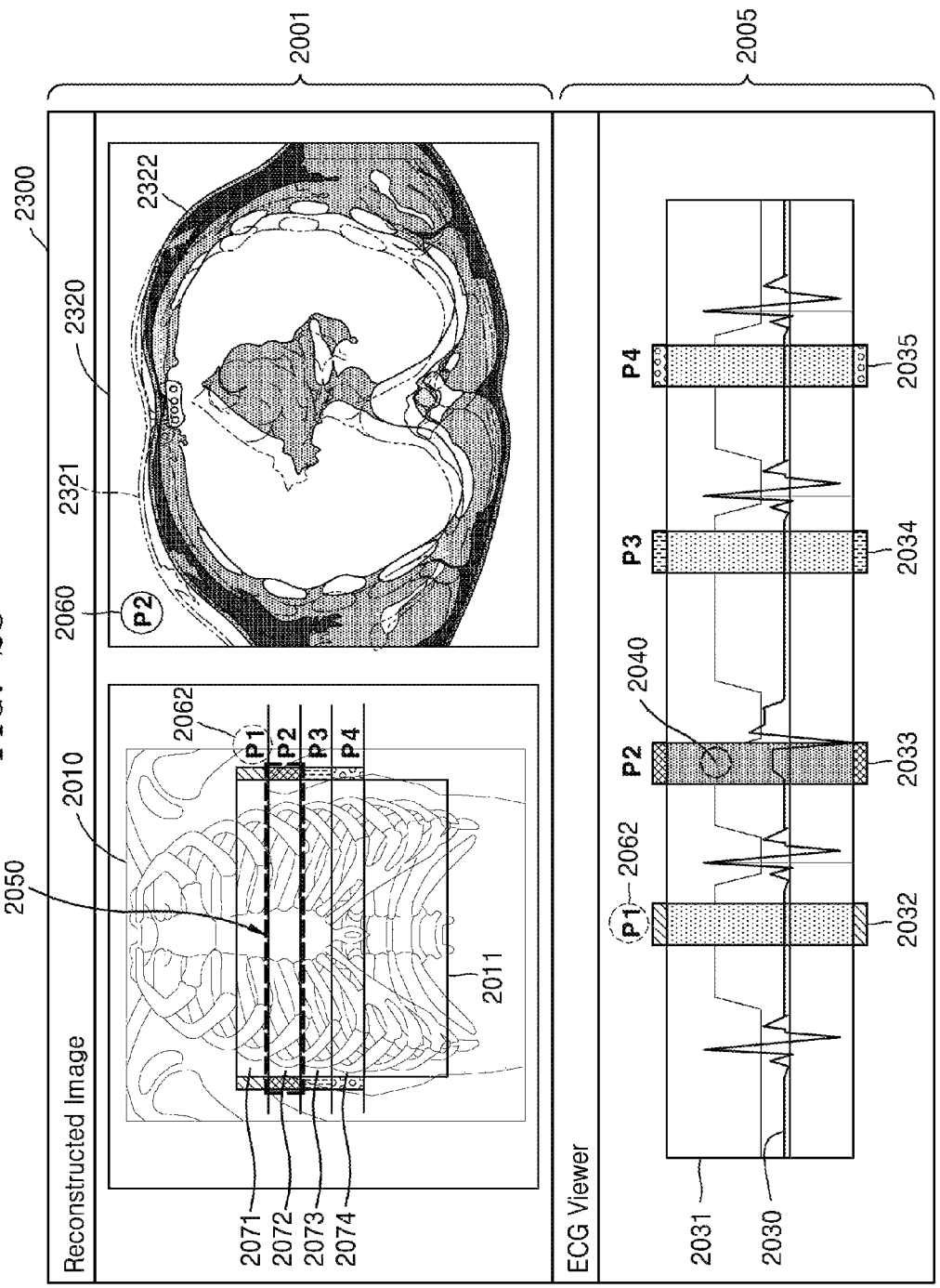
FIG. 23 illustrates another screen image displayed by the tomography apparatus according to an exemplary embodiment.

FIG. 23 illustrates a screen image 2300 displayed by the display 230 under the control of the image processor 220. The screen image 2300 of FIG. 23 corresponds to the screen image 2000 of FIG. 20A, and images and reference characters that are the same as those in FIG. 20A are repeated in FIG. 23. Thus, a repeated description thereof will be omitted.

As illustrated in FIG. 23, a section of the predetermined area 2011 on which a tomography image reconstruction is currently being performed may be indicated by a highlight 2050 and displayed on the screen image 2300.

The screen image 2300 may display a currently reconstructed cross-sectional tomography image included in the second image section 2072 that is currently being reconstructed by the image processor 220, on a predetermined area 2320. For example, a currently reconstructed cross-sectional tomography image 2322 with which a previously reconstructed cross-sectional tomography image 2321 is overlaid may be displayed on the predetermined area 2320. For example, the previously reconstructed cross-sectional tomography image 2321 may be indicated by a dotted line, and the currently reconstructed cross-sectional tomography image 2322 may be indicated by a solid line.

Accordingly, a user may easily recognize whether mismatch exists between the previously reconstructed cross-sectional tomography image 2321 and the currently reconstructed cross-sectional tomography image 2322. For example, if a stair artifact is generated, mismatch between the previously reconstructed cross-sectional tomography image 2321 and the currently reconstructed cross-sectional tomography image 2322 increases. Accordingly, if a big mismatch is generated between the cross-sectional tomography image 2321 and the currently reconstructed cross-sectional tomography image 2322, a user may determine that a stair artifact has been generated, and may take a measure, such as resetting of a partial period or interruption of a CT scan and image reconstruction.

Figure 24:
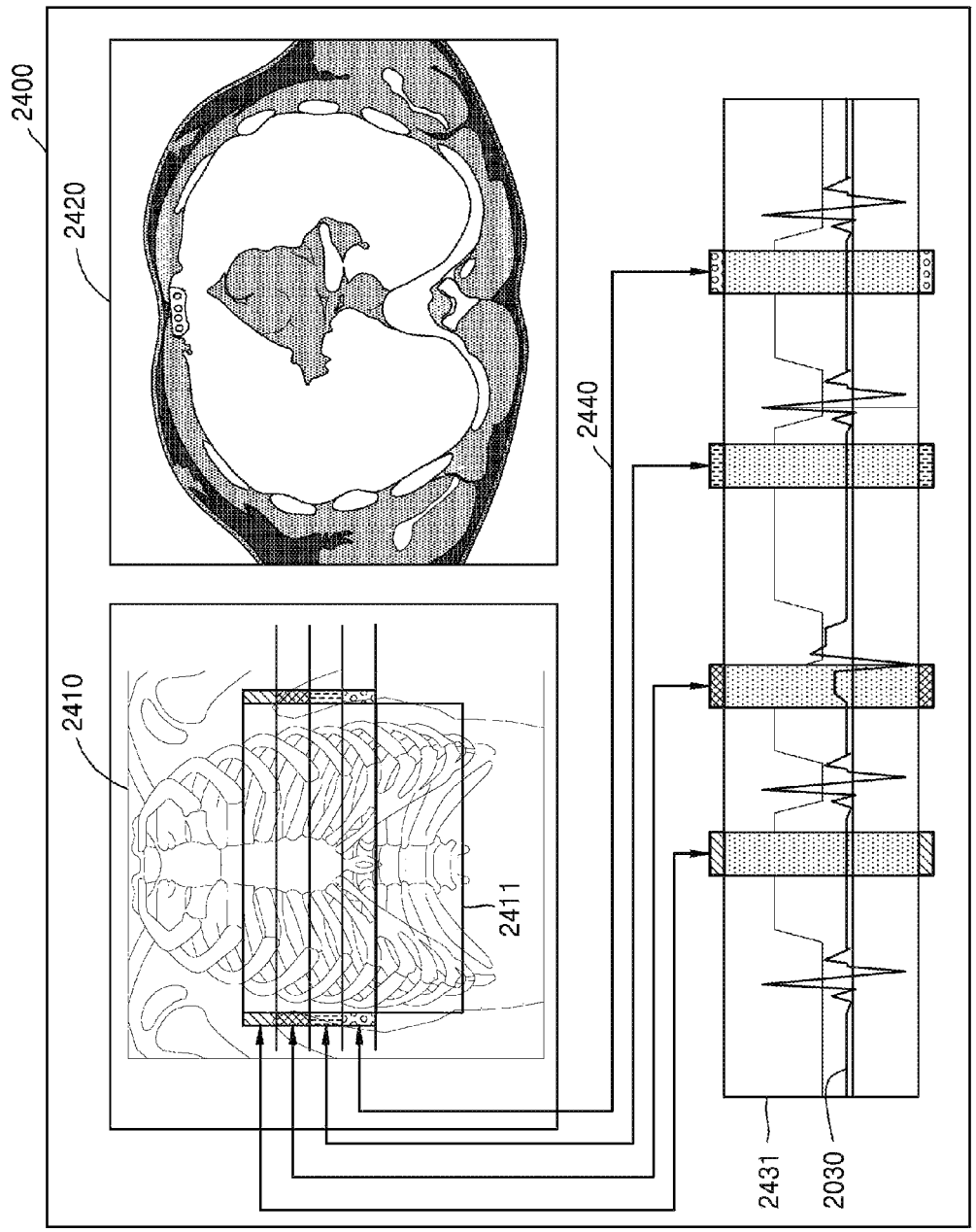
FIG. 24 illustrates another screen image displayed by the tomography apparatus according to an exemplary embodiment.

FIG. 24 illustrates a screen image 2400 displayed by the display 230 under the control of the screen image processor 220. A medical image 2410, a partial image 2420, and heartbeat period information 2431 of FIG. 24 may be the same as the medical image 2010, the partial image 2020, and the heartbeat period information 2031 of FIG. 21, respectively. Thus, a repeated description thereof will be omitted.

Referring to FIG. 24, when a plurality of partial periods and sections of a predetermined region 2411 corresponding to the partial periods are displayed in association with each other on the screen image 2400, the association may be visualized by connection lines 2440.

Figure 25A:
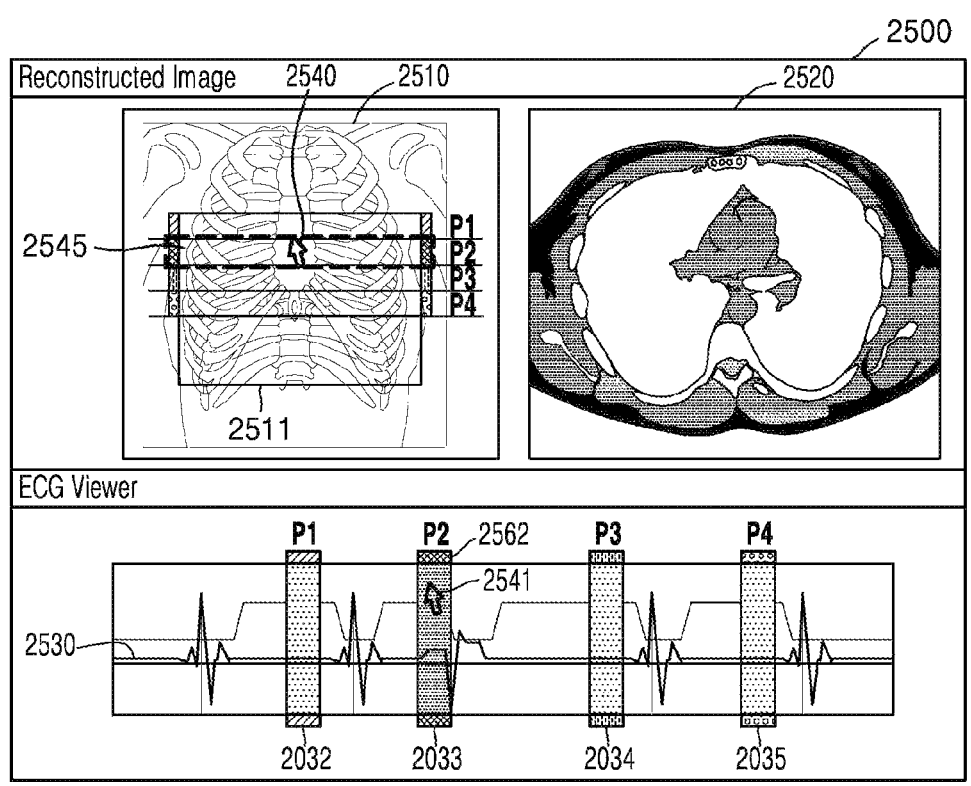
FIGS. 25A and 25B illustrate other screen images displayed by the tomography apparatus according to an exemplary embodiment.
Figure 25B:
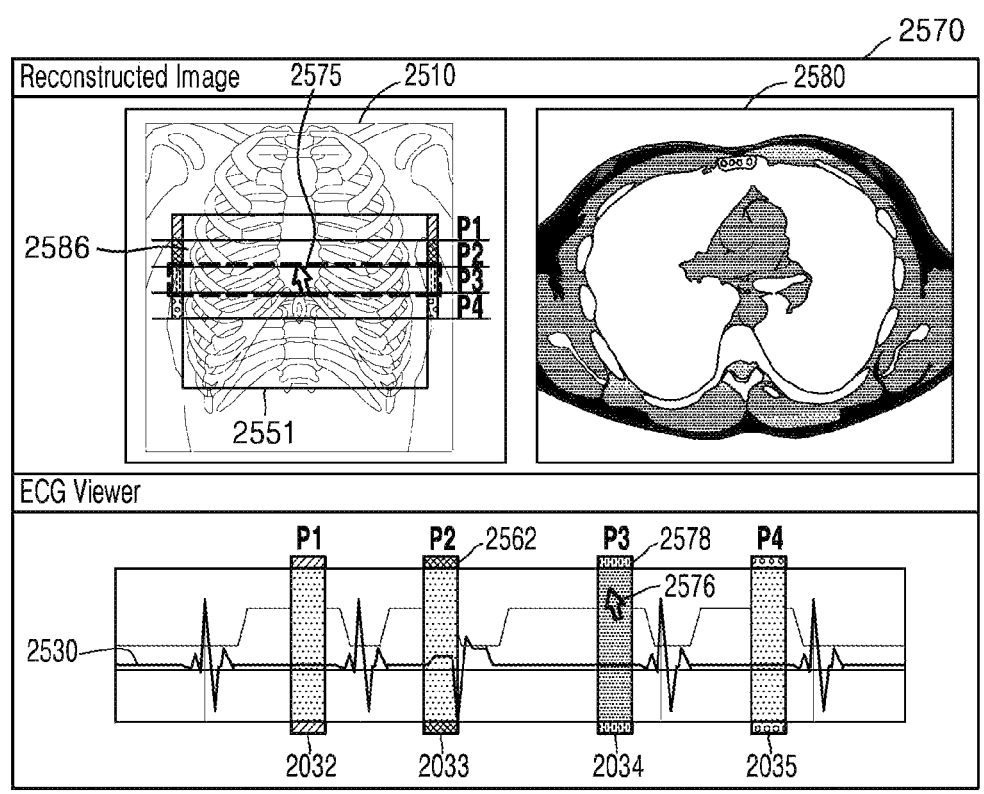

FIGS. 25A and 25B illustrate images 2500 and 2570, respectively, displayed by the display 230 under the control of the image processor 220.

The UI unit 240 may receive a user input of selecting a predetermined portion or point of a predetermined region 2511 or a predetermined partial period from among a plurality of partial periods of a heartbeat period.

Then, the image processor 220 may control a tomography image corresponding to the selected predetermined portion or point or the selected predetermined partial period in a reconstructed tomography image to be displayed on the screen image 2500.

Referring to FIG. 25A, when a user selects an image section 2545 within a predetermined region 2511 by using a cursor 2540, a cross-sectional tomography image 2520 included in the selected image section 2545 may be displayed. When a user selects a point within the predetermined region 2511 by using the cursor 2540, a cross-sectional tomography image 2520 corresponding to a cross-section of the selected point may be displayed.

When a user selects a P2 partial period 2562 of an ECG signal 2530 by using a cursor 2541, at least one sectional tomography image 2520 of a cross-sectional tomography image reconstructed using image data acquired during the P2 partial period 2562 may be displayed on the screen image 2500.

Referring to FIG. 25B, when a user changes a selection of a partial period or an image section via a UI, at least one partial image 2580 corresponding to a newly selected partial period or section image may be displayed on the screen image 2570.

For example, when the user selects another image section 2586 by using a cursor 2575, at least one reconstructed partial image 2580 corresponding to the selected image section 2586 may be displayed on the screen image 2570. When the user selects a P3 partial period 2578 of the ECG signal 2530 by using a cursor 2576, a partial image 2580 reconstructed using image data acquired during the selected P3 partial period 2578 may be displayed on the screen image 2570.

Figure 26:
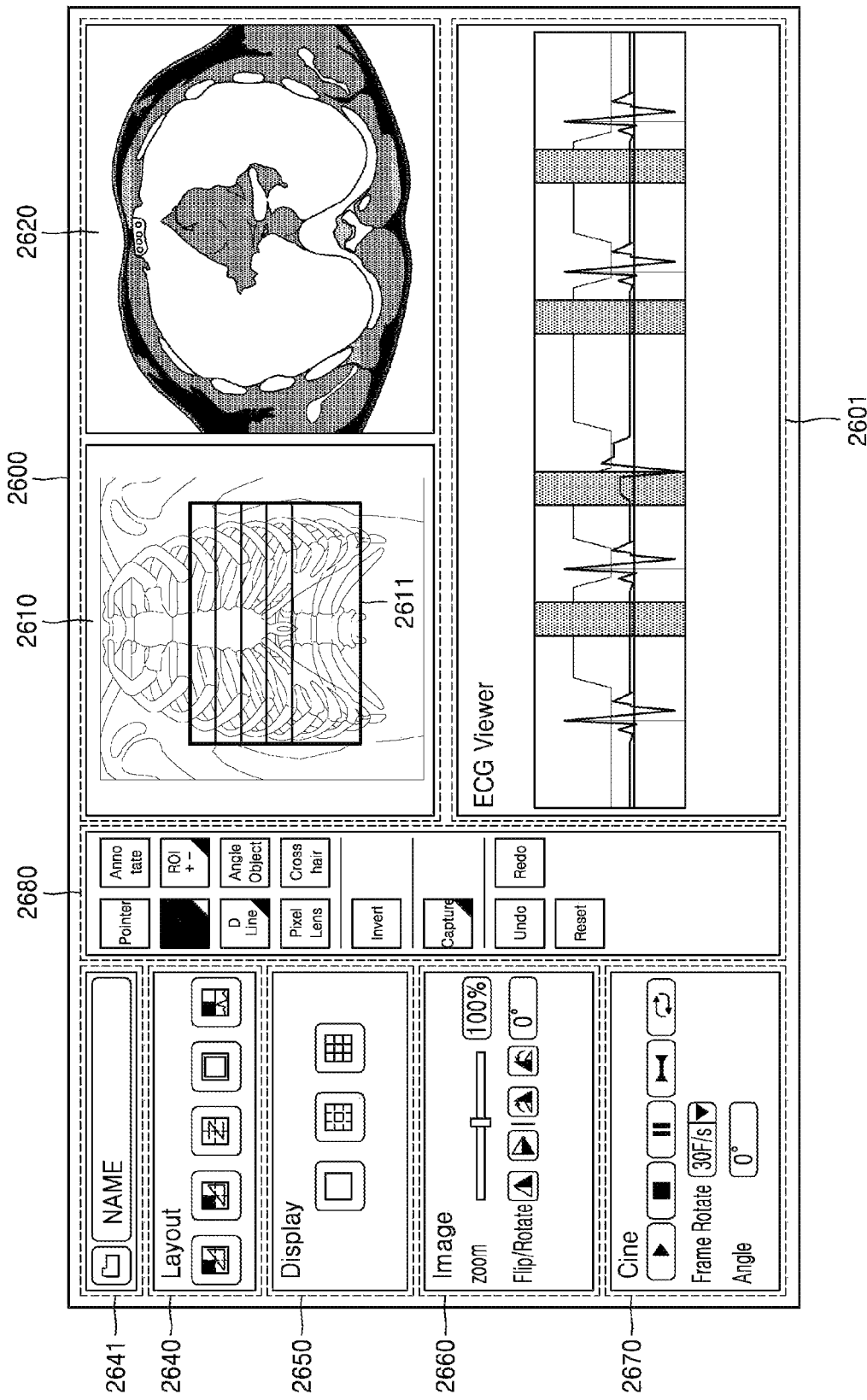
FIG. 26 illustrates another screen image displayed by the tomography apparatus according to an exemplary embodiment.

FIG. 26 illustrates a screen image 2600 displayed by the display 230 under the control of the image processor 220. A portion 2601 of FIG. 26 is the same as a portion of the information 2031 representing a heartbeat period in each of the screen images 2000, 2100, 2200, 2300, and 2400 of FIGS. 20A-24, and thus a repeated description thereof will be omitted.

Referring to FIG. 26, the screen image 2600 may include information 2641 about a patient, and at least one of various image edition menus. For example, personal information, such as the name of the patient, a medical history of the patient, items of check for previous medical images of the patient, the identification (ID) of the patient, and the like may be included in the information 2641 about the patient.

Examples of the image edition menus may include the image edition menu 2640 for setting a layout of an screen image 2600, the image edition menu 2650 for setting a display grid of the medical image 2610 or the partial image 2620, the image edition menu 2660 for image transformation of the medical image 2610 or the partial image 2620 included in the screen image 2600, the image edition menu 2670 for configuring a cine by using a reconstructed image, and the image edition menu 2680 for adjusting ROI settings or the like on the screen image 2600.

By using the image edition menus, a medical image more conforming to a user's intention may be generated.

Figure 27:
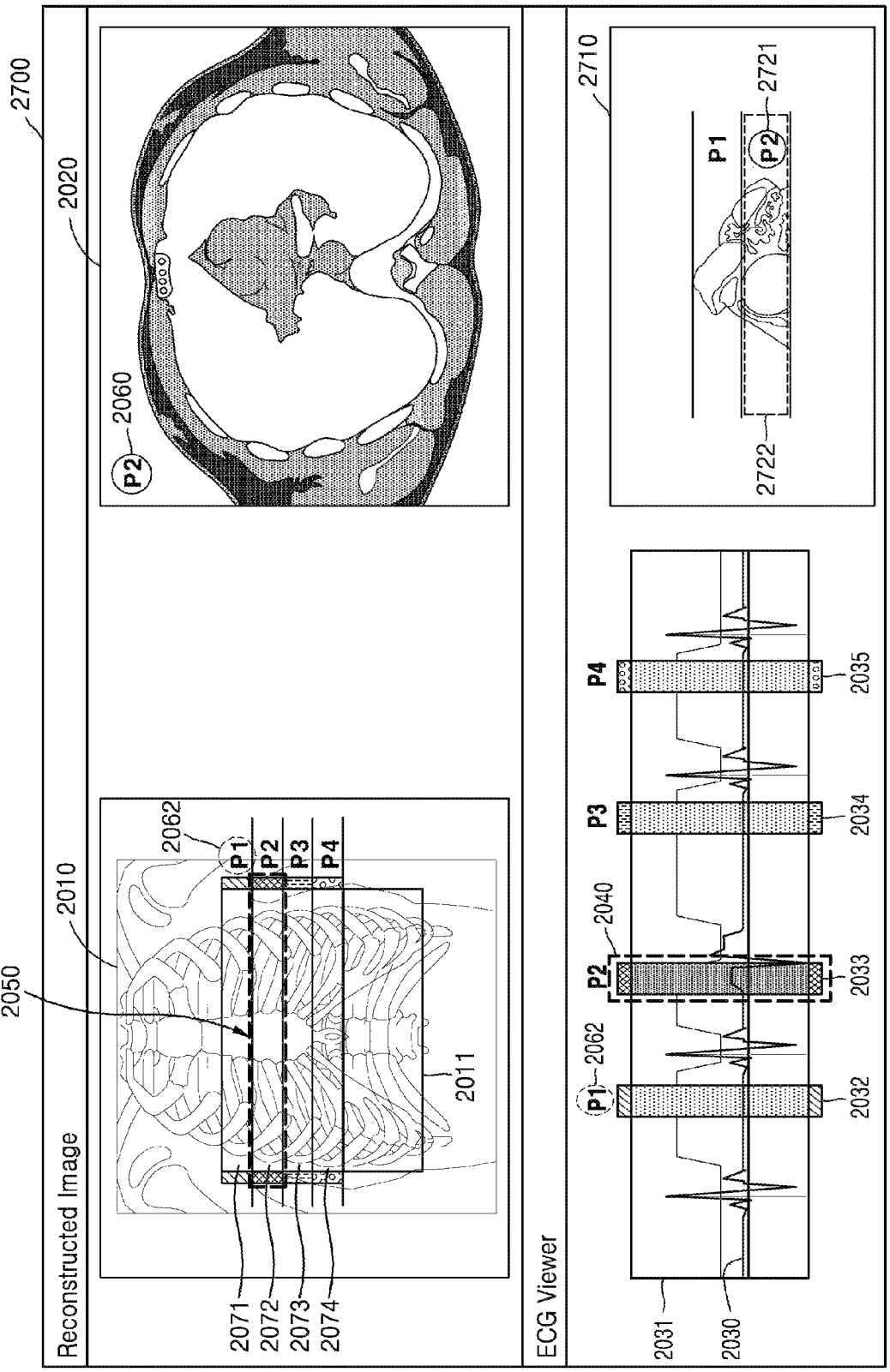
FIG. 27 illustrates another screen image displayed by the tomography apparatus according to an exemplary embodiment.

FIG. 27 illustrates another screen image displayed by the tomography apparatus according to an exemplary embodiment. Components of FIG. 27 that are the same as the components of FIG. 20A are indicated by the same reference numerals or characters. Thus, a repeated description thereof is omitted in the description of the components illustrated in FIG. 27.

Referring to FIG. 27, a screen image 2700 may further include a 3D tomography image 2710 that is reconstructed in real time, in addition to a medical image 2010, information 2031 representing a heartbeat period, and at least one partial image 2020.

The 3D tomography image 2710 may display a partial period corresponding to each image section such that the partial periods can be easily recognized. Referring to FIG. 27, a marker (e.g., a 'P2' marker 2721) indicating a partial period may be displayed for each image section of the 3D tomography image 2710. A highlight 2722 indicating an image section 2013 that is being currently reconstructed may be displayed.

Figure 28:
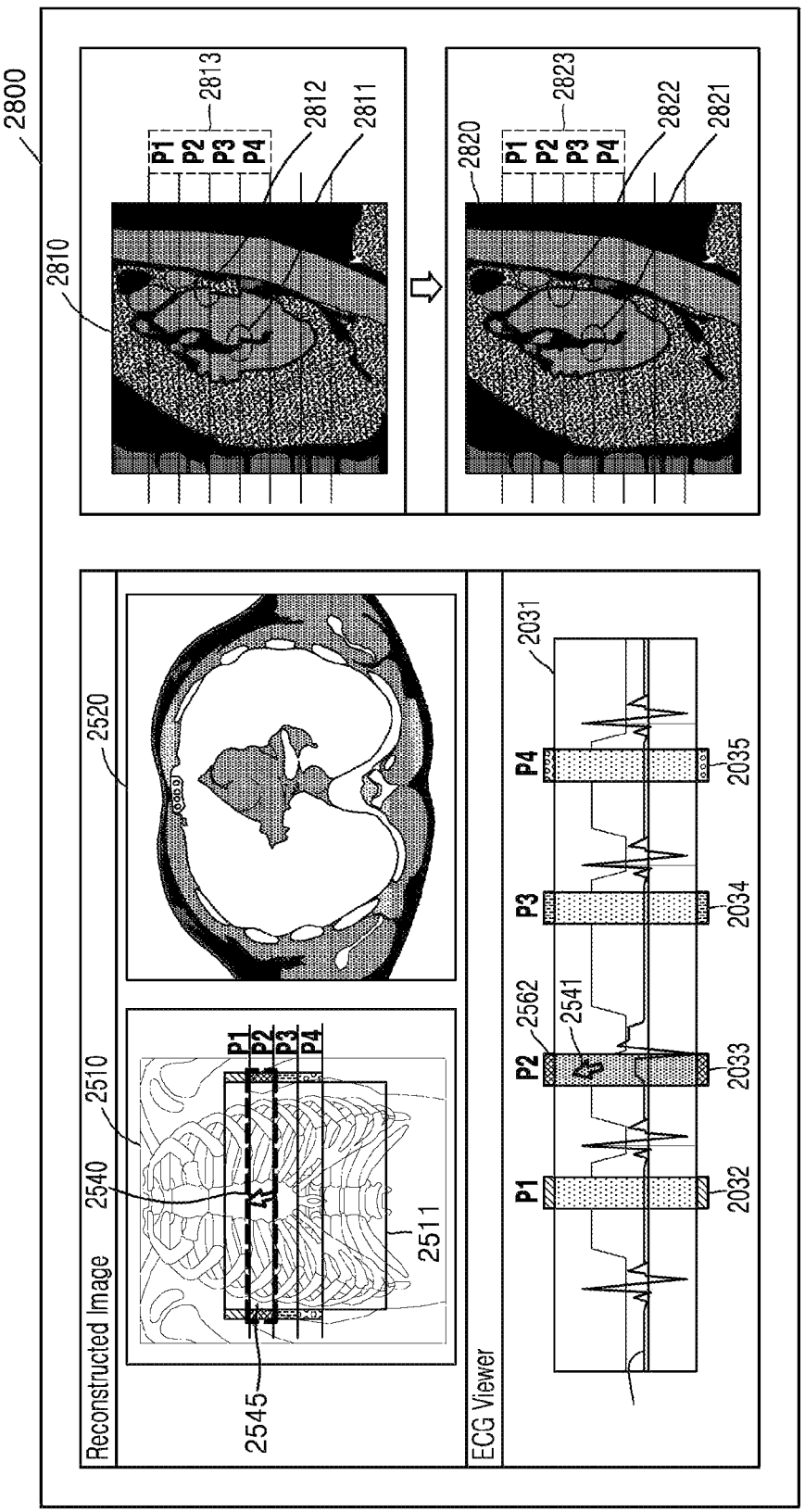
FIG. 28 illustrates another screen image displayed by the tomography apparatus according to an exemplary embodiment.

FIG. 28 illustrates another screen image displayed by the tomography apparatus according to an exemplary embodiment. Components of FIG. 28 that are the same as the components of FIG. 20A are indicated by the same reference numerals or characters. Thus, a repeated description thereof is omitted in the description of the components illustrated in FIG. 28.

Referring to FIG. 28, a screen image 2800 may further include an initially-reconstructed 3D tomography image 2810 and a corrected tomography image 2820, in addition to a medical image 2510, information 2031 representing a heartbeat period, and at least one sectional tomography image 2520. The initially-reconstructed 3D tomography image 2810 and the corrected tomography image 2820 may be the tomography image 1420 and the reconstructed-again tomography image 1460 of FIG. 14, respectively.

As described above, when a defect has been generated in the initially-reconstructed 3D tomography image 2810, the image processor 220 may correct the initially-reconstructed 3D tomography image 2810 so that the defect is removed from the initially-reconstructed 3D tomography image 2810. For example, the image processor 220 may reconstruct again a defect-containing image section by using re-setting of a period and data that is acquired during a re-set period. The image processor 220 may generate a corrected tomography image by correcting a defect-removed tomography image by performing image correction without resetting a period. The corrected tomography image 2820 may be a corrected tomography image or a reconstructed-again tomography image, which is obtained by the image processor 220. As illustrated in FIG. 28, stair artifacts 2811 and 2812 exist in the initially-reconstructed tomography image 2810, whereas the stair artifacts 2811 and 2812 may be removed from the corrected tomography image 2820 as in regions 2821 and 2822.

On the initially-reconstructed tomography image 2810 and the corrected tomography image 2820, which are included in the screen image 2800, image sections and partial periods of a heartbeat period may be displayed such that they are associated with each other. For example, markers 2813 and 2823 enabling a user to recognize heartbeat periods associated with the image sections may be displayed on the initially-reconstructed tomography image 2810 and the corrected tomography image 2820.

As described above, in a tomography apparatus and a tomography image displaying method performed by the tomography apparatus according to the one or more of exemplary embodiments, a heartbeat period is associated with a reconstructed image and the association is displayed. For example, in a tomography apparatus and a tomography image displaying method performed by the tomography apparatus according to the one or more of exemplary embodiments, at least one image section included in a reconstructed tomography image and a plurality of partial periods included in a heartbeat period are displayed such that they are associated with each other. Therefore, a data section used in reconstructing a tomography image may be intuitively ascertained. Accordingly, when a defect is generated in a reconstructed tomography image, a user may immediately ascertain a heartbeat period during which data used to reconstruct a defect-containing image section of the reconstructed tomography image is acquired. Therefore, the user may take immediate measures to correct the defect generated in the reconstructed tomography image, leading to a reduction in the time taken to acquire a final defect-free tomography image.

The exemplary embodiments can be written as computer programs and can be implemented in computers that execute the programs using a computer-readable recording medium.

Examples of the computer-readable recording medium include magnetic storage media (e.g., ROM, floppy disks, hard disks, etc.), optical recording media (e.g., CD-ROMs, or DVDs), etc.

The described-above exemplary embodiments and advantages are merely exemplary and are not to be construed as limiting. The present teaching can be readily applied to other types of apparatuses. The description of exemplary embodiments is intended to be illustrative, and not to limit the scope of the claims, and many alternatives, modifications, and variations will be apparent to those skilled in the art.

What is claimed is:

1. A tomography apparatus comprising:
an image processor configured to reconstruct a tomography image by using pieces of image data that are acquired during partial periods included in heartbeat periods; and
a display configured to display a screen image, which includes an image of the heartbeat periods, on which each of the partial periods is displayed between consecutive heartbeats, and the reconstructed tomography image, on which reconstructed image sections of respective partial periods are displayed in an association with the displayed respective partial periods,
wherein the association is displayed as graphics which visually associates each of the reconstructed image sections with at least one displayed respective partial period disposed between two consecutive heartbeats.

2. The tomography apparatus of claim 1, further comprising:
a monitor configured to acquire information representing a result of monitoring an electrocardiogram (ECG) signal representing the heartbeat periods.

3. The tomography apparatus of claim 2, wherein the image processor is configured to acquire the partial periods by windowing a phase section of the ECG signal by ECG gating and control the partial periods to be indicated by windows in the ECG signal and then displayed.

4. The tomography apparatus of claim 1, further comprising:
an information provider configured to inform a user of a defect in response to the defect being present in the reconstructed tomography image.

5. The tomography apparatus of claim 1, wherein the display is configured to display the screen including a marker on at least one selected from a defective partial period, which is included in the partial periods and corresponds to a defect, and a defect-containing image section of the reconstructed tomography image, which has been reconstructed in correspondence to the defective partial period, under the control of the image processor.

6. The tomography apparatus of claim 4, wherein, in response to a defect being present in the reconstructed tomography image, the image processor is configured to extract a defect-free partial period that would prevent generation of the defect in the reconstructed tomography image from one of the heartbeat periods, and control the display to display a user interface (UI) image for recommending the extracted defect-free partial period to a user.

7. The tomography apparatus of claim 6, further comprising:
a user interface (UI) unit configured to receive a selection of the recommended defect-free partial period via the UI image,
wherein the image processor is configured to reconstruct again an image portion corresponding to the defect-containing image section by using the pieces of image data acquired during the selected defect-free partial period.

8. The tomography apparatus of claim 1, wherein, in response to a defect being present in the reconstructed tomography image, the image processor is configured to automatically adjust a defective partial period corresponding to the defect, and automatically correct a defect-containing image section by using the pieces of image data acquired during the adjusted partial period.

9. The tomography apparatus of claim 1, further comprising:
a user interface (UI) unit configured to output a menu for selecting another partial period instead of a defective partial period corresponding to a defect-containing image section of the reconstructed tomography image, and receive a selection of the another partial period via the menu,
wherein the image processor is configured to automatically correct the defect-containing image section by using the pieces of image data acquired during the selected another partial period.

10. The tomography apparatus of claim 1, wherein the image processor is configured to acquire pieces of projection data during the partial periods, reconstruct the partial images by using the pieces of projection data, and generate a final tomography image representing an object by using the partial images.

11. The tomography apparatus of claim 1, wherein the tomography image is a three-dimensional (3D) tomography image.

12. The tomography apparatus of claim 1, wherein the image processor acquires an initially reconstructed tomography image that is obtained based on the pieces of image data, and generates a final tomography image by correcting a defect generated in at least one image section included in the initially reconstructed tomography image.

13. The tomography apparatus of claim 12, wherein the screen image further comprises the final tomography image.

14. The tomography apparatus of claim 12, wherein a tomography image included in the screen image is the initially reconstructed tomography image and the final tomography image.

15. A tomography apparatus comprising:
an image processor configured to reconstruct a tomography image by using pieces of image data that are acquired during partial periods included in a heartbeat period, and, in response to a defect being present in the reconstructed tomography image, reconstruct again an image portion corresponding to a defect-containing image section of the reconstructed tomography image by using corrected image data acquired during another partial period which avoids a defect generation; and
a display configured to display a screen image including the reconstructed tomography image including image sections, update the defect-containing image section of the reconstructed tomography image with the corrected image data, and display an updated image section corresponding to a result of the updating.

16. The tomography apparatus of claim 15, wherein, in response to the defect being present in the reconstructed tomography image, the image processor is configured to acquire position information of the another partial period, from the heartbeat period, and acquire the corrected image data based on the position information.

17. The tomography apparatus of claim 15, wherein the display is configured to display the screen image, which includes information representing the heartbeat period and the reconstructed tomography image and on which an image section of the reconstructed tomography image that corresponds to at least one of the partial periods is displayed in association with the at least one partial period.

18. The tomography apparatus of claim 15, wherein the display is configured to display the screen image on which the updated image section is visually distinguished from the image sections which have not been updated.

19. The tomography apparatus of claim 15, wherein the display is configured to display a marker which identifies the updated image section on the screen image.

20. The tomography apparatus of claim 15, wherein the display is configured to display the screen image which includes information representing the heartbeat period, and
the corrected partial period is marked within the information representing the heartbeat period, on the screen image.

21. The tomography apparatus of claim 20, wherein the display is configured to display the screen image on which the partial period corresponding to the defect is visually distinguished from the another partial period within the information representing the heartbeat period.

22. The tomography apparatus of claim 15, further comprising:
a user interface (UI) unit configured to output a menu image for recommending the another partial period and receive a selection of the recommended another partial period via the menu image, in response to the defect being present in the reconstructed tomography image.

23. The tomography apparatus of claim 22, wherein the image processor is configured to reconstruct again an image portion corresponding to the defect-containing image section by using the corrected image data acquired during the selected another partial period and generate an updated tomography image.

24. The tomography apparatus of claim 15, further comprising:
a monitor configured to acquire information representing a result of monitoring an electrocardiogram (ECG) signal representing the heartbeat period.

25. A tomography image displaying method comprising:
reconstructing a tomography image by using pieces of image data that are acquired during partial periods included in heartbeat periods; and
displaying a screen image that includes an image of the heartbeat periods, on which each of the partial periods is displayed between consecutive heartbeats, and the reconstructed tomography image, on which reconstructed image sections of respective partial periods are displayed in an association with the displayed respective partial periods,
wherein the association is displayed as graphics which visually associates each of the reconstructed image sections with at least one displayed respective partial period disposed between two consecutive heartbeats.

26. The tomography image displaying method of claim 25, further comprising:
ascertaining that a defect has been generated in the reconstructed tomography image;
extracting, from one of the heartbeat periods, a defect-free partial period that prevents generation of a defect in the reconstructed tomography image, in response to the defect generated in the reconstructed tomography image; and
outputting a user interface (UI) image for recommending the extracted defect-free partial period to a user.

27. The tomography image displaying method of claim 25, further comprising:
automatically adjusting a defective partial period corresponding to a defect-containing image section, in response to a defect being present in the reconstructed tomography image; and
automatically correcting the defect-containing image section by using the pieces of image data acquired during the adjusted partial period.

28. A tomography image displaying method comprising:
reconstructing an initial tomography image by using pieces of image data that are acquired during partial periods included in a heartbeat period;
displaying a screen image including the reconstructed initial tomography image;
reconstructing again an image portion corresponding to a defect-containing image section of the reconstructed initial tomography image by using corrected image data acquired from another partial period which would prevent generating a defect, in response to the defect being present in the reconstructed initial tomography image;
updating the defect-containing image section with a reconstructed-again image portion; and
displaying a result of the updating.

29. A tomography apparatus comprising:
an image processor configured to reconstruct a tomography image corresponding to a predetermined region of a medical image including an object, by using pieces of image data that are acquired during partial periods included in heartbeat periods; and
a display configured to display a screen image, which includes an image of the heartbeat periods on which each of the partial periods is displayed between consecutive heartbeats, and the medical image including the predetermined region on which image sections of respective partial periods are displayed in an association with the displayed respective partial periods,
wherein the association is displayed as graphics which visually associates each of the image sections with at least one displayed respective partial period disposed between two consecutive heartbeats.

30. The tomography apparatus of claim 29, wherein the screen image further comprises a sectional tomography image included in the reconstructed tomography image.

31. The tomography apparatus of claim 30, wherein the reconstructed tomography image is a transverse cross-sectional tomography image.

32. The tomography apparatus of claim 30, wherein the medical image is a scout image that represents an entire object, and
the sectional tomography image is a cross-sectional image included in the reconstructed tomography image.

33. The tomography apparatus of claim 32, wherein the scout image is an anteroposterior or a lateral scout image, and
the sectional tomography image is a transverse cross-sectional tomography image.

34. The tomography apparatus of claim 30, wherein the screen image visually associates the sectional tomography image with an image section of the predetermined region that corresponds to the sectional tomography image.

35. The tomography apparatus of claim 30, wherein the screen image visually associates the sectional tomography image with a respective partial period corresponding to the sectional tomography image.

36. The tomography apparatus of claim 30, further comprising:
a user interface (UI) unit configured to receive an input of at least one among the predetermined portion or a point selected from the predetermined portion and a partial period selected from the partial periods,
wherein the image processor is configured to control the display to display, on the screen image, a tomography image included in the reconstructed tomography image that corresponds to the selected point or the selected partial period.

37. The tomography apparatus of claim 30, wherein, as the tomography image is being reconstructed, the reconstructed tomography image is updated and an updated tomography image is displayed on the screen image.

38. The tomography apparatus of claim 37, wherein the screen image visually associates the updated tomography image with an image section of the predetermined region that corresponds to the updated tomography image.

39. The tomography apparatus of claim 37, wherein the screen image visually associates the updated tomography image with one of the partial periods corresponding to the updated tomography image.

40. The tomography apparatus of claim 37, wherein a current tomography image that is the updated tomography image and a previous tomography image that is reconstructed prior to the updated tomography image are displayed on the screen image so that the previous tomography image is overlaid with the current tomography image.

41. The tomography apparatus of claim 29, wherein the screen image further comprises a 3D tomography image corresponding to the reconstructed tomography image, and the screen image shows the partial periods and image sections included in the 3D tomography image that correspond to the partial periods in an association with each other.

42. The tomography apparatus of claim 1, wherein the image of the heartbeat periods with the displayed partial periods, the reconstructed tomography image with the displayed reconstructed image sections, and the graphics association are all displayed together on the screen image.

* * * * *